(12) United States Patent
Hanley et al.

(10) Patent No.: US 11,418,831 B2
(45) Date of Patent: Aug. 16, 2022

(54) SYSTEM AND METHOD FOR IMMUTABLE VIRTUAL PRE-SITE STUDY

(71) Applicant: SIGNANT HEALTH GLOBAL LLC, Blue Bell, PA (US)

(72) Inventors: Mark Hanley, Scottsdale, AZ (US); Daniel Bouganim, Agoura Hills, CA (US)

(73) Assignee: SIGNANT HEALTH GLOBAL LLC, Blue Bell, PA (US)

( * ) Notice: Subject to any disclaimer, the term of this patent is extended or adjusted under 35 U.S.C. 154(b) by 0 days.

(21) Appl. No.: 17/210,000

(22) Filed: Mar. 23, 2021

(65) Prior Publication Data

US 2021/0297723 A1     Sep. 23, 2021

Related U.S. Application Data

(60) Provisional application No. 62/993,537, filed on Mar. 23, 2020.

(51) Int. Cl.
*H04N 21/422* (2011.01)
*H04N 21/4363* (2011.01)

(52) U.S. Cl.
CPC . *H04N 21/42222* (2013.01); *H04N 21/43637* (2013.01)

(58) Field of Classification Search
CPC ... H04N 5/247; H04N 21/4524; H04N 5/2251
See application file for complete search history.

(56) References Cited

U.S. PATENT DOCUMENTS

| | | | |
|---|---|---|---|
| 8,893,247 B1 * | 11/2014 | Faaborg | G06F 21/6245 726/7 |
| 2006/0085731 A1 | 4/2006 | Cui et al. | |

(Continued)

FOREIGN PATENT DOCUMENTS

WO     2001-025938 A1     4/2001

OTHER PUBLICATIONS

Kobayashi et al., "Exploratory Application of Augmented Reality/Mixed Devices for Acute Care Procedure Training," Western Journal of Emergency Medicine 19.1 (2018): 158. Dec. 14, 2017 (Dec. 14, 2017) Retrieved on May 24, 2017 (May 24, 2017) from <https://www.ncbi.nlm.nih.gov/pmc/articles/PMC5785186/> entire document.

(Continued)

*Primary Examiner* — Samira Monshi
(74) *Attorney, Agent, or Firm* — Hogan Lovells US LLP

(57) ABSTRACT

Virtual site inspections to support clinical trials is disclosed. A frame and glasses subsystem has at least a global positioning system (GPS) and is associated with a first computing device at a physical site where an inspection is conducted. A session is opened in a web-based application on a second communication device that is in communication with, but that is physically remote from, the first computing device. Location tracking using GPS allows for a location of the frame and glasses subsystem to be continuously tracked. A script from the web-based application to the first computing device enables association with a video stream and locations within the physical site. The script enables responses to be provided from the first computing device at the locations. The locations, time stamps, video stream, the responses from the script, and a device identifier is provided immutably to the web-based application.

18 Claims, 16 Drawing Sheets

(56) References Cited

U.S. PATENT DOCUMENTS

| | | |
|---|---|---|
| 2010/0114594 A1 | 5/2010 | Schultz |
| 2013/0083011 A1 | 4/2013 | Geisner et al. |
| 2017/0076043 A1 | 3/2017 | Dormer et al. |
| 2020/0005938 A1* | 1/2020 | Sloan .................... G16H 80/00 |

OTHER PUBLICATIONS

International Search Report and Written Opinion dated Jun. 23, 2021, corresponding to PCT/US2021/023711.

* cited by examiner

SYSTEM AND METHOD FOR IMMUTABLE VIRTUAL PRE-SITE STUDY

CROSS-REFERENCE TO RELATED APPLICATION(S)

This application is related to and claims the benefit of priority from U.S. Provisional Application No. 62/993,537, filed Mar. 23, 2020, titled SYSTEM AND METHOD FOR PRE-SITE STUDY VISIT PROCEDURES FOR CLINICAL RESEARCH TRIALS, the entire disclosure of which is incorporated by reference herein for all intents and purposes.

BACKGROUND

1. Field of Invention

This invention relates in general to clinical research trial systems and methods, and in particular, to interfaces for such clinical research trial systems.

2. Description of the Prior Art

Clinical trials are part of clinical research and constitute the heart of medical advances. Clinical trials look at innovative methods to prevent, detect, or treat diseases. Treatments may include new drugs, new surgical procedures, new devices, or new ways to use existing treatments. A goal achieved in such clinical trials is to ascertain whether a new treatment works, is safe for administering, and has potential to improve the quality of life for people with illnesses addressable by such new treatment.

Clinical trials that support Federal Drug Administration (FDA) approvals for new drugs involve substantial costs. Such cost can extend even further for certain drug development processes. Pharmaceutical companies in the United States include costs of critical clinical trials in its processes for FDA approvals of new drugs. Inclusion of costs from critical clinical trials adds to a final high cost associated with drug development, because it also includes costs associated with the drug development activity itself. Furthermore, studies, including those for drug discovery, can be time-consuming and can range from 6 months to 10 years.

Pharmaceutical companies may contract with research sites, such as, doctors' offices and hospitals to conduct such clinical trials. However, before expending money and time to conduct such trials, pharmaceutical companies ensure that a research site is sufficient to undertake demands associated with such trials. To ensure sufficiency of one or more research sites, a Clinical Research Associate (CRA) conducts a pre-site study visit (PSSV), which can include a tour of the research site, interviews with a study coordinator and physician, and other items that may be defined by a checklist. Such a checklist is required to be completed to conclude a pre-site study visit. Other items for a checklist may also include verification (and inventory) of equipment at each research site, temperature logs at the research site, and any and all standard operating procedures (SOPs) in place.

A Pre-Selection Site Visit (PSSV) can take between two to four hours at each research site. Such time may not include travel and preparation required by a CRA. With a traditional model for PSSV, it can take, on average, between six to eight months for clinical trials to commence. About an initial 3-month portion of such time may be dedicated to a PSSV. With a shortage of CRAs and with multiple projects having different target dates, research sites may not have key questions answered to enable determination of whether they can successfully enroll a clinical trial. Furthermore, CRAs may have to travel to the sites and have to schedule a PSSV in accordance with schedules of physicians, study coordinators, and all other key players who must attend an PSSV, and who may not be able to do so. Still further, information communicated between parties during a PSSV are disconnected or discretized pieces of data without features for association at inspection points of a research site, without underlying features to provide evidentiary support that specific inspection was actually performed, and without features that dissuades change to such pieces of information or that maintains confidentiality.

SUMMARY

At least one embodiment described below addresses issues raised in the above sections to enable immutable virtual pre-site study while keeping information communicated between parties during a PSSV properly coordinated to each inspection point at a research site and retained with immutability and confidentiality.

In at least one embodiment, a system for immutable virtual pre-site study to support clinical trials is disclosed. Such a system includes a frame and glasses subsystem that may further include at least a global positioning system (GPS) and a camera and may include at least one processor and memory having instructions that when executed by the at least one processor cause the system to perform certain functions or actions. A function caused includes opening of a session in a web-based application for the system. In at least one embodiment, such a session may be associated with an immutable virtual pre-site study, which may represent an immutable virtual PSSV. The immutable virtual pre-site study may be conducted using a first computing device linked to the session and that may be associated with the frame and glasses subsystem, at a physical location of an immutable virtual PSSV. Location tracking, using the GPS, may be enabled for a location of the frame and glasses subsystem during the immutable virtual pre-site study. Transmission of a script is enabled from the web-based application to the first computing device, which is remote from a second computing device interfacing with the web-based application. Such a script may be associated with a video stream from the camera and with a location of the frame and glasses subsystem. Display of such a script is enabled along with the video stream for a first computing device using GPS tracking of the video stream and target insertion points within the script, so as to enable questions at certain locations of a pre-site visit and to enable responses from the first computing device. Immutable association is enabled of two or more of locations, time stamps, the video stream, the responses to the script, and a device identifier, in the first computing device.

In at least one embodiment, a method for method for immutable virtual pre-site study to support clinical trials is also disclosed. Such a method is enabled in a system provided with a frame and glasses subsystem in association with at least a global positioning system (GPS) and a camera. The method includes opening a session in a web-based application, where the session may be associated with an immutable virtual pre-site study using a first computing device that is linked to the session and that is associated with the frame and glasses subsystem. Location tracking is enabled in the method, using the GPS, for a location of the frame and glasses subsystem during the immutable virtual pre-site study. Transmission is enabled for a script, from the web-based application to the first computing device that is remote from a second computing device interfacing with the web-based application. The script may be associated with a video stream from the camera and with the location. The script is displayed with the video stream for the first computing device and enables generation of responses from the first computing device. Immutable association is enabled of two or more of locations, time stamps, the video stream, the responses to the script, or a device identifier, in the first computing device.

BRIEF DESCRIPTION OF THE DRAWINGS

Various embodiments in accordance with the present disclosure will be described with reference to the drawings, in which.

DETAILED DESCRIPTION

Figure 1:
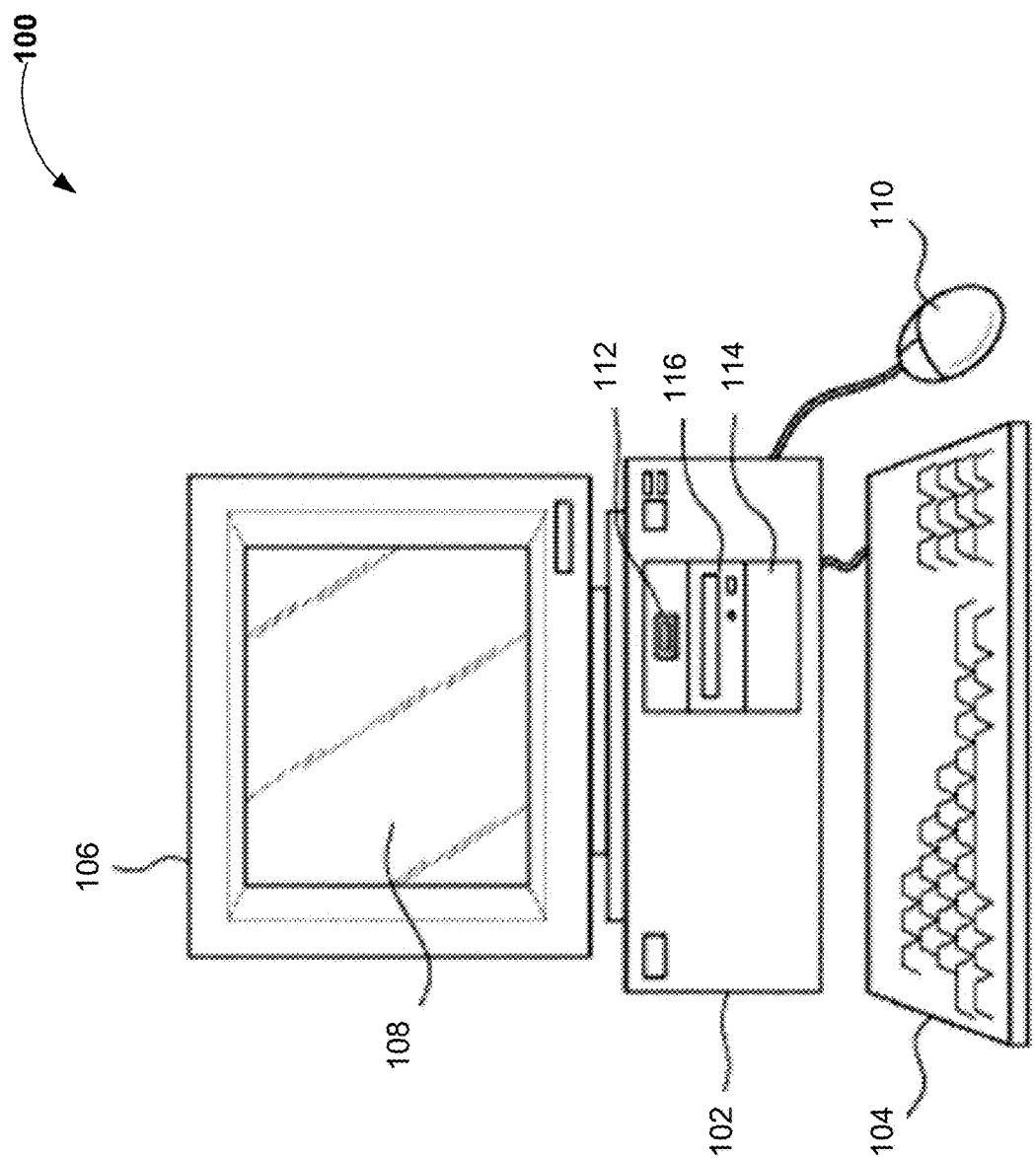
FIG. 1 illustrates a computer system configured for use with at least one embodiment herein.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Various other functions can be implemented within the various embodiments as well as discussed and suggested elsewhere herein. In at least an aspect, the present disclosure is to a system and a method for immutable virtual pre-site study.

In at least one embodiment, system features (such as hardware) along with software (either as an application or firmware) enable or allow real-time exchange and storage of an immutable virtual PSSV information. Such exchange may include immutable association of two or more pieces of information provided to a first computing device at a physical site, such as a research site associated with an immutable virtual PSSV. All information related to a physical site required for an immutable virtual PSSV may be exchanged between at least the first computing device, a frame and glasses subsystem, and a web-based application interfacing with a second computing device that may be remote from the first computing device and from the frame and glasses subsystem.

A system that tracks and records discrete data may be unable to provide verification across the different data (and associated data types, such as video, audio, location, and text scripts), except that they are independently gathered and independently interfaced to and from a user of such a system. In at least one embodiment, a system and method herein may associate discrete pieces of information from different sources using, for example, time stamps and GPS-tracked location, during a site visit, and target insertion points in a script having the questions. Such a feature also enables a script to be associated with a video stream, in real-time, during a pre-site visit using GPS locations and enables responses at certain time stamps, all of which are immutably stored. In at least one embodiment, such an association is beneficial in a specific application of discretized data for pre-site visits, where specific discretized data (video stream, location, questions, and responses) is rigorously verified, associated, and stored in an immutable manner.

The system and method may support verification requirements for pre-site visits in real-time, such that questions intended for certain inspection actions (for example, at certain locations at a research site) may be presented for responses, and their responses received for immutable storage in an associated manner with the questions, locations, and time stamps. A verification requirement for a pre-site visit may include association between a location determined via GPS of specific equipment in a research site that is determined as related to a target insertion point stated in a script having the questions. Such association may be an immutable association between discrete data by location tags (such as target insertion points and/or GPS data), time stamps (at such a location associated to the data), and read-only storage of such data. The system and method may further include an ability to receive a script and associate such a script to a video stream in real time, along with securing responses to questions within a script at locations during a pre-site visit, providing benefits over purely discrete data otherwise received.

The system and method also enable appropriate questions (such as relating to a specific equipment or area in a research site) to be displayed on a first computing device in coordination with a frames and glasses subsystem. As a study monitor or CRA is located remotely from a site coordinator, such a feature addresses an inability of a CRA or study monitor to physically track a study coordinator, but to still secure a verified and fully answered pre-site visit. Thus, verification that the specific equipment was inspected during the pre-site visit can be obtained.

The frame and glasses subsystem used in the inspection system and method disclosed herein may be in near-field proximity communication with the first computing device that then communicates with the web-based application of a remote second computing device. The system and method herein is therefore able to track locations, time stamps, an audio stream, a video stream, responses to a script, and a device identifier, and is able to formalize this information for a web-based application. This at least reduces time and cost for newly formed entities to conduct their an immutable virtual PSSVs virtually. Such an immutable virtual pre-site study includes providing a study coordinator (remote from a CRA) with smart glasses that form a frame and glasses subsystem and that may be associated with a camera. A system and method of an immutable virtual pre-site study allows such a study coordinator to be embedded at a research site in advance of an immutable virtual PSSV, and then enables immutable retrieval and use of information from a research site.

A study coordinator equipped with such a frame and glasses subsystem is able to move around a research site and is able be linked (via the first computing device) with a session of a web-based application associated with a second computing device of a CRA. A first computing device at a research site may be in near-field proximity communication, using Bluetooth®, or even broader range but local communication such as Wi-Fi®, with a frame and glasses subsystem. In turn, the first computing device may be linked to a web-based session opened using a web-based application of a second computing device. This enables a secure portal between a study coordinator and a CRA located remotely from a study coordinator. In at least one embodiment, this allows a web-based application to host multiple distinct sessions to prevent cross-contamination of data from different research sites.

The study coordinator, moving around with a frame and glasses subsystem is able to show a CRA, who is located off-site (or remotely from the study coordinator, all items on a script that may be provided to the first computing device. The script may include a pre-site checklist, such as to check a pharmaceutical refrigerator, temperature logs, centrifuge, exam room, and other aspects required for an immutable virtual PSSV. The CRA can view any image or video stream in a similar time frame and view as a study coordinator. As the study coordinator is looking at certain views in real-time, an image (such as frames of vides) of the views may be streamed to a CRA's computer screen (on a second computing device). This enables a CRA to verify that a research site has sufficient equipment and space to conduct a research study.

Furthermore, such a process may require immutable association of two or more pieces of information sent to a first computing device at a physical site. Two or more of time stamps, scripts, responses, and locations, or device identifiers may be required to be combined and locked to prevent improper changes. Metadata, encryption, or distributed ledgers may be used to enable immutable association of two or more pieces of such information. This enables credibility for the information from an immutable virtual PSSV returned to web-based application and accessible to a second computing device. The information may be further loaded to a cloud computing environment and the session itself may be opened on a cloud computing environment using virtual or physical computing devices that may be transparent to users of the first computing device and of the second computing device.

There may be circumstances where travel is impeded by a CRA, directly to a research site, but that approval of an underlying drug or device is important. In a recent example, the Center for Disease Control (CDC) in the United States discouraged travel in order to deter spread of a virus during a pandemic (such as spread of COVID-19). However, approval of a vaccine for such a virus is also extremely important and time-sensitive. More so, in a pandemic, where time is crucial in the area of drug development, pharmaceutical companies have limited time and resources to expend in aspects that are away from drug development. Such rationing of time must be assisted by expedited and proper clearances, such as enabled by a system and method for an immutable virtual pre-site study visit procedure. In an example, CRAs may be sent to research cites, in person, to review setups for clinical trials and to ensure credibility of information, but this is a costly, time-consuming, and imperfect solution that may also cost human lives, especially during a pandemic.

A PSSV physically conducted in person by a CRA can take about three months to complete and can be very expensive if considered for every pre-site visit. However, the system and method for an immutable virtual pre-site study described herein is able to support remote sessions and immutable association, transmission, and storage of data so that around 75 immutable virtual PSSVs may be completed in two weeks. Thus, conducting site visits and inspections using the system and method described herein maintains credibility of information gathered while reducing costs that would otherwise be incurred to send a CRA to a plurality of sites to conduct physical, in-person inspections. The system and method for an immutable virtual pre-site study allows pharmaceutical companies to allocate costs to other crucial areas of drug development. In addition, the system and method can save pharmaceutical companies time required for conducting the PSSVs. Still further, once credibility of information is achieved, drugs or treatment plans may be approved in a timelier manner.

A CRA may be a health-care professional who performs many activities related to medical research, particularly clinical trials. Further, CRAs work in various settings, such as pharmaceutical companies, medical research institutes, and government agencies. A Pre-Site Study Visit or an immutable virtual PSSV refers to a requirement that, before a sponsor awards a clinical trial to a site, a sponsor (such as a CRA) conduct a pre-site study visit. An immutable virtual PSSV may be designed to help sponsors select qualified investigators and to help determine a research site's ability to conduct a clinical trial. To be selected, study coordinators may first be qualified by training and by education and experience. Moreover, a research site must have adequate resources, staffing, and facilities that may be necessary to conduct a study as proposed.

A study coordinator is in reference to a person who coordinates an immutable virtual PSSV with other participants at the site and a remote CRA during a session on a web-based application, such as a virtual site monitoring application (or a virtual immutable virtual PSSV application). A virtual site monitoring application may be a stand-alone or browser-based mobile or computer-application that may be configured to be part of a system and method for an immutable virtual pre-site study. Participants or other participants referred to herein may include CRAs, physicians, study coordinators, or other individuals and entities given access to one or more session(s) of a web-based application (such as an immutable virtual PSSV session in the virtual site monitoring application) or and that may be involved in a clinical research trial.

FIG. 1 illustrates an example environment 100 subject to improvements of at least one embodiment herein. As shown in FIG. 1, a computer system may be an example environment 100 and reference number 100 is interchangeably used to reflect this. A computer system 100 may be improved by inclusion of at least software adapted to perform features as detailed herein. All of or a portion of such a computer system 100 may be used to implement a web-based application adapted to open a session in a web-based application so that the session may be associated with the immutable virtual pre-site study using a first computing device that is linked to the session and that is associated with the frame and glasses subsystem. A computer system 100, as shown in FIG. 1, may also be used as a second computing device that may allow a first computing device and other computing devices to join such a session opened via its web-based application.

A system for a virtual immutable pre-site study includes at least one processor and memory, such as storage modules. In at least one embodiment, one or more chassis 102 (and its internal components) may be used to implement part or all of one or more embodiments of a system and method for immutable virtual pre-site study that is detailed herein. One or more elements of computer system 100 (such as, a monitor 106, a keyboard 104, and/or a mouse 110) may also be used to implement part of all of one or more embodiments of the system and methods described herein.

Computer system 100 may include chassis 102 that includes one or more circuit boards, a Universal Serial Bus (USB) port 112, a Compact Disc Read-Only Memory (CD-ROM) and/or Digital Video Disc (DVD) drive 116, and a hard drive 114. One or more circuit boards may include at least one processor to execute instructions stored on associated memory to perform function disclosed throughout herein. Elements included, either partly or fully, on one or more circuit boards inside chassis 102 are further illustrated in FIG. 2.

Figure 2:
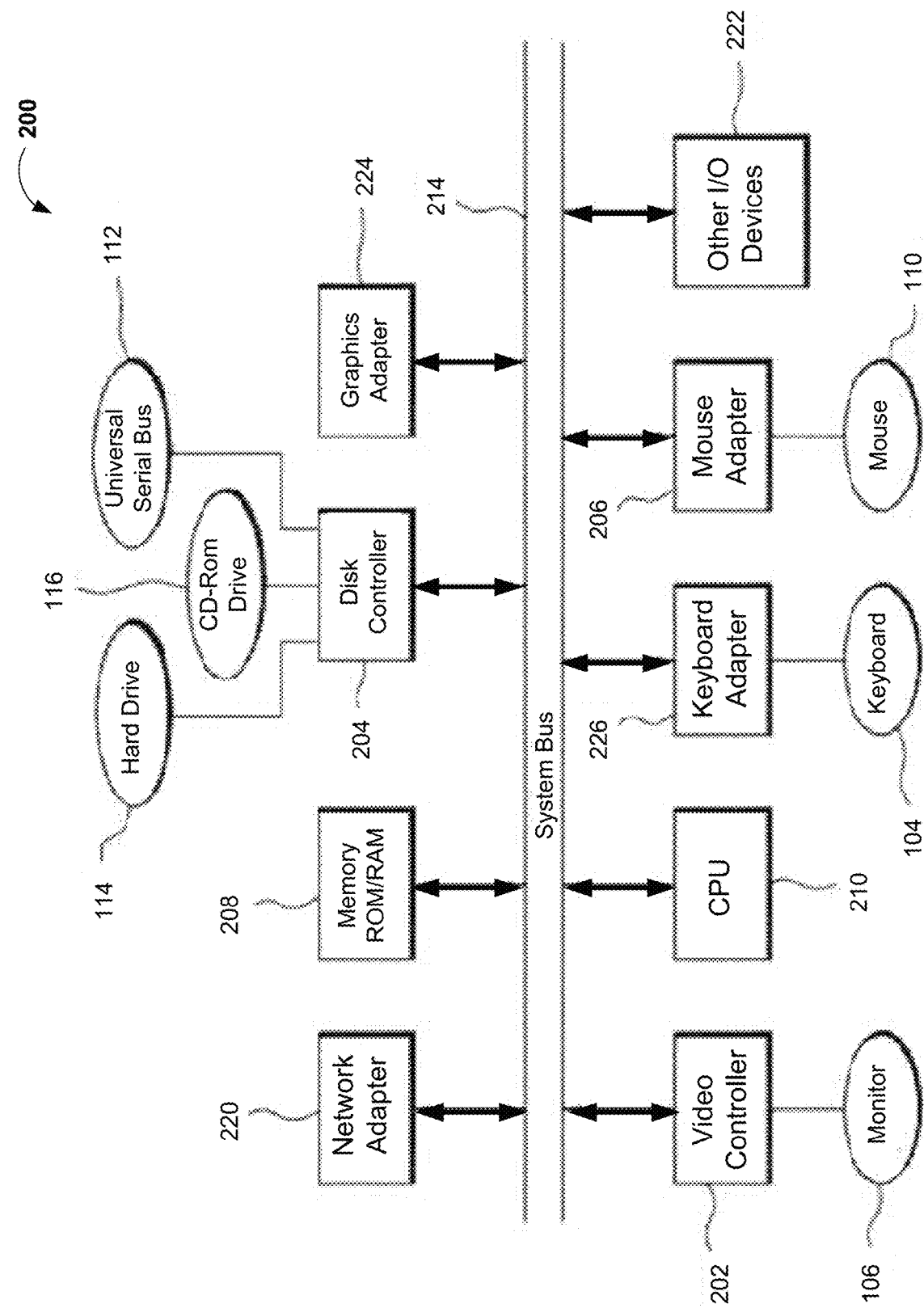
FIG. 2 illustrates further details of a computer system configured for use with at least one embodiment, that is subject to improvements of at least one embodiment herein.

As shown in FIG. 2, at least one processor may be a central processing unit (CPU) 210, which may be coupled to a system bus 214. An architecture of CPU 210 may be compliant with any of a variety of commercially distributed architecture families but may be adapted to provide a system for immutable virtual pre-site study by executing code or instructions from memory associated with CPU 210. The system bus 214 may be coupled to memory of a second computing device 100. In at least one embodiment, such memory is a memory storage unit 208 and may include (i) volatile memory, such as, for example, random access memory (RAM) and/or (ii) non-volatile memory, such as, for example, read only memory (ROM). A non-volatile memory can be removable and/or non-removable non-volatile memory. RAM-type memory may include dynamic RAM (DRAM) and static RAM (SRAM). ROM-type memory may include mask-programmed ROM, programmable ROM (PROM), one-time programmable ROM (OTP), erasable programmable read-only memory (EPROM), electrically erasable programmable ROM (EEPROM) (such as, electrically alterable ROM (EAROM) and/or flash memory).

The memory storage module(s) may include memory storage unit 208 and an external memory storage drive. An external memory storage device may be a USB-equipped electronic memory storage drive coupled to a universal serial bus (USB) port 112 (as illustrated in FIGS. 1-2), hard drive 114 (also as illustrated in FIGS. 1-2), CD-ROM and/or DVD drive 116 (also as illustrated in FIGS. 1-2), a floppy disk drive, an optical disc, a magneto-optical disc, and magnetic tape. Furthermore, non-volatile or non-transitory memory storage module(s) refer to the portions of the memory storage module(s) that are non-volatile (and may include non-transitory type) memory.

Portions of the memory storage module(s) of the various embodiments disclosed herein (such as portions of the non-volatile memory storage module(s)) may be embedded with a boot code sequence suitable for restoring computer system 100 to a functional state after a system reset. In addition, portions of the memory storage module(s) of the various embodiments disclosed herein (such as portions of the non-volatile memory storage module(s)) can comprise microcode such as a Basic Input-Output System (BIOS) operable with computer system 100. Portions of a memory storage module(s) may include an operating system, which can be a software program that manages hardware and software resources of a computer system 100 and/or a computer network.

A BIOS can initialize and test components of computer system 100 and can load such an operating system. An operating system can perform basic tasks such as, controlling and allocating memory, prioritizing the processing of instructions, controlling input and output devices, facilitating networking, and managing files. Additional instructions may be included to support features for an immutable virtual pre-site study, include to enable secure connectivity to a cloud environment and to enable secure communications with other devices associated with a session opened using the computer system 100.

Other operating systems may be used with a computer system 100 and an application for an immutable virtual pre-site study may be implemented on such other operating systems, including on one of the following types of operating system: (i) Microsoft® Windows® operating system (OS) by Microsoft Corp. of Redmond, Wash., United States of America, (ii) Mac® OS X by Apple Inc. of Cupertino, Calif., United States of America, (iii) UNIX® OS, and (iv) Linux® OS. Further exemplary operating systems can comprise one of the following: (i) the iOS® operating system by Apple Inc. of Cupertino, Calif., United States of America, (ii) the Blackberry® operating system by Research In Motion (RIM) of Waterloo, Ontario, Canada, (iii) the WebOS operating system by LG Electronics of Seoul, South Korea, (iv) the Android™ operating system developed by Google, of Mountain View, Calif., United States of America, (v) the Windows Mobile™ operating system by Microsoft Corp. of Redmond, Wash., United States of America, or (vi) the Symbian™ operating system by Accenture PLC of Dublin, Ireland.

The least one processor and/or a processing module may be any type of computational circuit, such as but not limited to a microprocessor, a microcontroller, a controller, a complex instruction set computing (CISC) microprocessor, a reduced instruction set computing (RISC) microprocessor, a very long instruction word (VLIW) microprocessor, a graphics processor, a digital signal processor, or any other type of processor or processing circuit capable of performing the desired functions. Further, one or more processing modules disclosed herein may include a CPU 210.

FIG. 2 also illustrates various I/O devices such as a disk controller 204, a graphics adapter 224, a video controller 202, a keyboard adapter 226, a mouse adapter 206, a network adapter 220, and other I/O devices 222 can be coupled to system bus 214. A keyboard adapter 226 and mouse adapter 206 are coupled to keyboard 104 and mouse 110, respectively, of computer system 100. While a graphics adapter 224 and video controller 202 are indicated as distinct units in FIG. 2, video controller 202 can be integrated into graphics adapter 224, or vice versa. A video controller 202 may be suitable for monitor 106 to display reports and images on a screen 108 of a computer system 100. Further, a disk controller 204 can control a hard drive 114, a USB port 112, and a CD-ROM drive 116. However, distinct units may be used to control each of these devices separately.

FIG. 2 also illustrates a network adapter 220 that may be used to connect a computer system 100 to a computer network by wired communication (such as, a wired network adapter) and/or wireless communication (such as, a wireless network adapter). A network adapter 220 may be plugged or coupled to an expansion port in computer system 100. Alternatively, a network adapter 220 may be built into computer system 100. In at least one embodiment, a network adapter 220 may be built into a computer system 100 by being integrated into one or more circuit boards, such as a motherboard chipset. Still further, a network adapter may be implemented via one or more dedicated communication chips, connected through a PCI (peripheral component interconnector), or connected via a PCI express bus of computer system 100 or through a USB port 112. Many other components of computer system 100 and their interconnection may be understood to those of ordinary skill in the art upon reading the present detailed description.

When a computer system 100 is running, program instructions (such as, computer instructions) stored on one or more of the memory storage module(s) of the various embodiments disclosed herein can be executed by at least one processor, such as by CPU 210. At least a portion of the program instructions (or plainly, instructions), may be stored on such devices, and may be used for implementing a system and method for an immutable virtual pre-site study.

A computer system 100 may have a different form factor while still having functional elements similar to those described throughout this detailed description. In at least one embodiment, a computer system 100 may include a single computer, a single server, or a cluster or collection of computers or servers, or a cloud of computers or servers. Such further system detail is illustrated in at least FIGS. 3 and 14. A cluster or collection of servers may be used when demand on a computer system 100 exceeds a reasonable capability of a single server or computer. A computer system 100 may also include a portable computer, such as a laptop computer, in a different form factor than illustrated. A computer system 100 may also include a mobile electronic device, such as a smartphone or a tablet. A computer system 100 may comprise an embedded system as well. Furthermore, a first computing device used at a physical site may include one or more such computer systems but may be mobile versions to support movement of a study coordinator at a research site.

Figure 3:
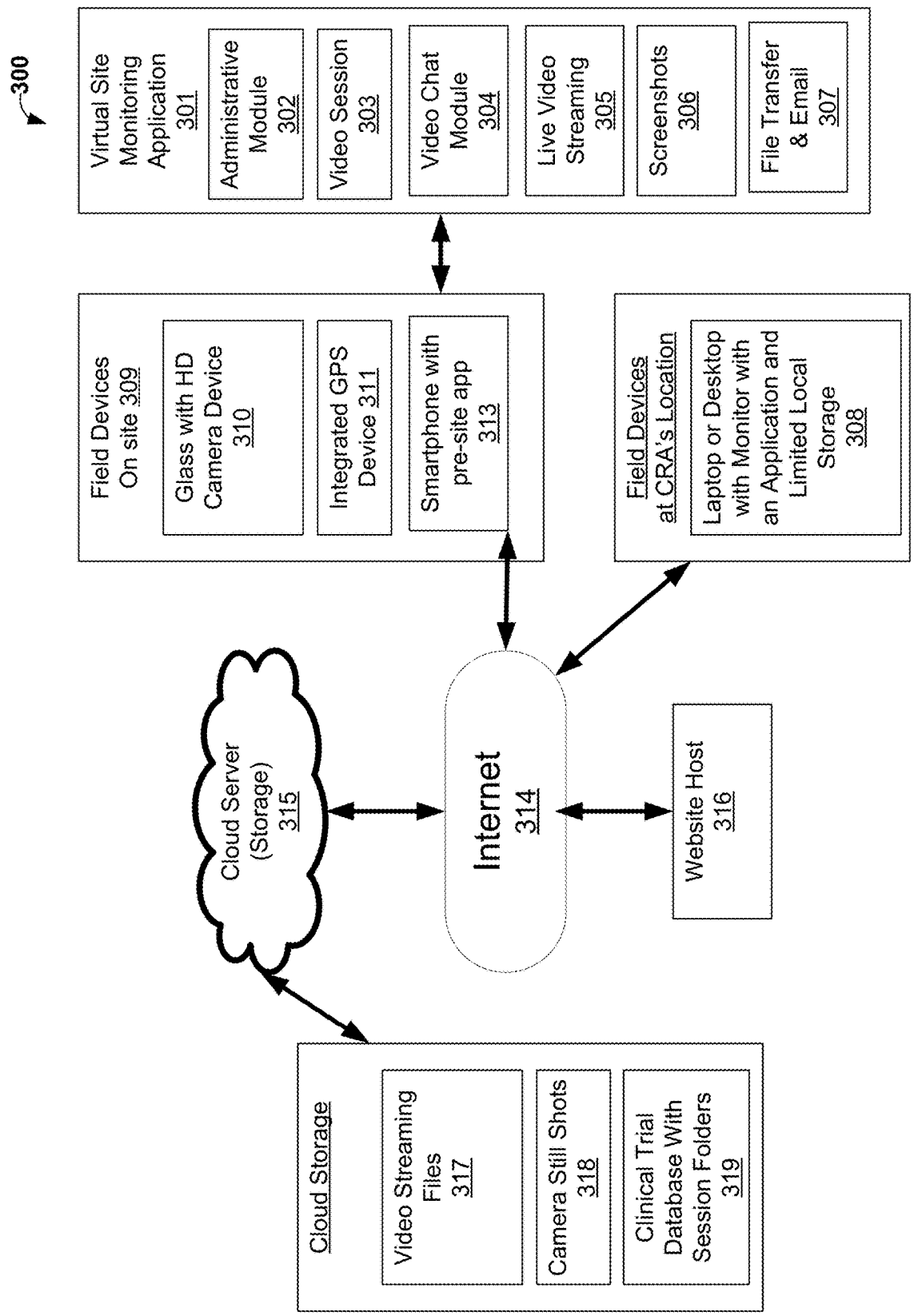
FIG. 3 illustrates aspects of a system for an immutable virtual pre-site study according to at least one embodiment herein.

FIG. 3 illustrates aspects of a system 300 for an immutable virtual pre-site study according to at least one embodiment herein. Further, system 300 may be adapted for an immutable virtual pre-site study to support clinical trials. System 300 may include a computer system 100 and other components adapted to enable hardware and/or software to function cooperatively. System 300 may therefore include at least one processor and memory having instructions that when executed by the at least one processor cause the system 300 to perform functions that enable an immutable virtual pre-site study.

In at least one embodiment, a CRA and/or clinical research trial participant can use a laptop or desktop with a monitor, such as the computer systems described in FIG. 1 and FIG. 2. Further, a CRA may use field devices at a CRA's location 308. A CRA's location may be remote from a research site but may also be remote from other components required to enable a system 300 for immutable virtual pre-site study. A CRA's field device may include a computer system (such as a computer system 100) with limited local storage 308. The CRA's location and the field devices of the CRA's location are interchangeably referenced by the same numeral reference 308.

A CRA's field device may be a second computing device as described throughout herein. Such a second computing device communicates with at least one field device at the research site 309. As such, at least one field device at a research site and the research site itself are interchangeably referenced by the same reference numeral 309. The field devices at the research site 309 include one or more first computing devices, and may be used by a study coordinator when conducting the site inspection. The second computing device 308 may be used to open a session in a web-based application, such as a virtual site monitoring application 301 that may have a front-end provided by a website host 316. Such as session may be associated with an immutable virtual pre-site study using a first computing device (physically at a research site 309) that is linked to the session and that is associated with the frame and glasses subsystem.

A first computing device may be joined to the session after permission is granted by a second computing device. The session may be hosted on a cloud server that has its own storage 315. A network, such as the internet 314, may be used to enable the first computing device and the second computing device to communicate. A website host 316 may be used to provide aspects of a web-based application. As such, a web-based application 301 may be a collective feature of one or more computing devices that are collectively referred to as a second computing device that interface with a web-based application. The first computing device may be physically remote from the one or more computing devices interacting over the web-based application 301. Moreover, a session may be collectively a secure communication channel, a secure website, a secure webpage, and a secure storage system.

In at least one embodiment, a web-based application system 301 may be a virtual site monitoring application or a virtual site monitoring application for system 300. The virtual site application system 301 may include an administrative module 302, configured to permit a CRA and participants of the clinical research trial or site inspection to store information regarding scheduling and appointments, such as on-demand appointments, for the PSSV. The system or application may support a video session 303 capable of retrieving an audio and video stream from a frame and glasses subsystem 310. The frame and glasses subsystem 310 includes capability for a high definition (HD) video stream using a camera device, which may be integrated with or contained within the frame and glasses, or may be connected thereto. The camera device coordinates with a first computing device at a research site 309 to start capturing a video stream. The first computing device located at the research site 309 may be a smartphone 313 that executes instructions for part of an immutable virtual pre-site study. In at least one embodiment, such instructions may be package as an application for the smartphone 313.

A GPS device 311 may be integrated into or associated with a frame and glasses subsystem that may be represented by a combination of reference numerals 310, 311. The PSSV application system 301, which includes an administrative module 302, video session capturing application 303, video chat module 304, live video streaming functionality 305, screenshot capturing and display module 306, and file transfer and communication module 307, may be provided at a research site 309 to enable a study coordinator to capture and stream video to a CRA computer system 308. The GPS 311 enables location tracking, upon instruction from elsewhere in system 300. In at least one embodiment, such location tracking may be for one or more locations of the frame and glasses subsystem during the immutable virtual pre-site study.

In conducting a site inspection, a study coordinator may use field devices on a research site 309 to stream video (or video data) to a web-based application, such as a virtual site monitoring application. In at least one embodiment, system 300, using a frame and glasses subsystem 310, with its HD streaming camera and integrated GPS device 311, may first communicate using near-field proximity communications, with a first computing device, which may be the smartphone having a virtual site monitoring mobile application (or virtual an immutable virtual PSSV mobile application) 313. Alternatively, the GPS device 311 can be included in the mobile device in communication with the frame and glasses subsystem. For example, when a smartphone executing the mobile application is in wired or wireless communication with the frame and glasses subsystem, a GPS device embedded with the smartphone may be used to provide GPS information that is associated with audio and video streams captured by the frame and glasses subsystem.

Moreover, audio may be captured by the smartphone and associated with the video streams captured by the fame and glasses subsystem. The study coordinator may wear the frame and glasses subsystem, which may be in wired or wireless communication with the mobile or computing device, such as a smartphone, executing a mobile application 313. In at least one embodiment, such a virtual site monitoring mobile application 313 is distinct from a web-based application or may be a component of such as web-based application. In at least one embodiment, a virtual site monitoring immutable associations from information in such data. In at least one embodiment, a virtual site monitoring application, different from the virtual site monitoring mobile application, may be executing at a second computing device 308.

A second computing device 308 may enable transmission of a script from a web-based application to a first computing device, such as to smartphone with its application 313. The first computing device 313 may be remote from a second computing device 308 (and may include 316) interfacing with the web-based application. The script may be generated using the second computing device 308 interfacing with a web-host 316 and a cloud storage having a database 319. For example, a script may be generated using a form creation application of a web-based application, as illustrated at least in FIGS. 13A-13C. Generated scripts may then be associated with a video stream from a camera of the frame and glasses subsystem and with the location tracked from a GPS 311. Where audio data is also to be captured, this audio data may additionally be associated with the script.

The camera or a first computing device may be enabled for filtering certain content in real-time. For example, the camera or a first computing device may be enabled for filtering the video stream for privacy protection of patient information if any patient information is exposed at a research site. Such filtering may be enabled by blurring of matter that is irrelevant to an immutable virtual PSSV. Matter that should be filtered may be determined beforehand and information and data in relation to a site inspection conducted may be subject to such a filter before being communicated to a first computing device. In at least one embodiment, faces may be blurred from either in-person subjects or photos posted anywhere in a field of view. Further, papers (or other printed material) may not be captured till express permission is provided by a study coordinator at a research site using a mobile application. Still further, when a study coordinator enters an area having a patient or patient information, the first computing device is able to execute instructions to blur a background associated with the patient. In addition, it is possible to automatically shut of any cameras and microphones till the study coordinator has cleared the area of patient information or till the study coordinator confirms that no patient information is visible.

Scripts for conducting the site inspections may be provided with an identifier so that it may be displayed on the smartphone (the first computing device 313) or other computing device of a study coordinator at an inspection site when it is determined, such as through GPS information, that the study coordinator is at the appropriate location. In an example, a script may include computer code or instructions, and questions for a study coordinator. The determination of an appropriate location may be made on the first computing device, or may be made by a second computing device 308 operated by a CRA at a remote location after receiving the GPS information. For example, when a study coordinator is at a specific location determined by a GPS as coinciding with an inspection action, a script may provide questions seeking responses associated with such an inspection action. The script may be formed out of a form creation application and may have sections for inspection actions, locations, and questions. Responses to the questions, audio data, video data, photographs, and other information captured in accordance with or in response to the script may be immutably associated with a time stamp, with a location, and with a device identifier. The time stamp may be from a video stream and/or an audio stream that may be synchronized at a later time or concurrently with being stored and transmitted to a cloud server 315.

Figure 6:
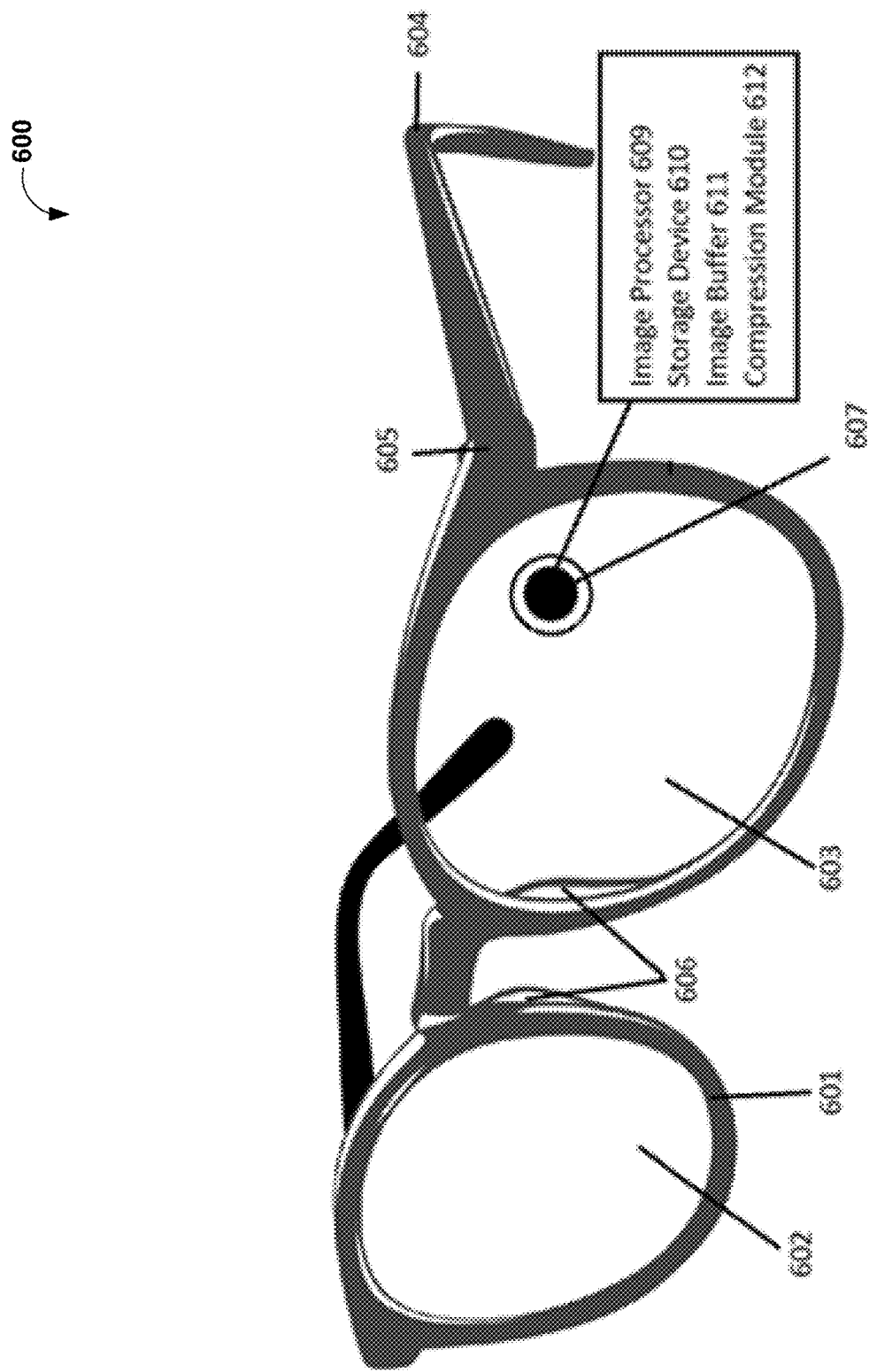
FIG. 6 illustrates a frame and glasses subsystem for an immutable virtual pre-site study according to at least one embodiment herein.

As noted above, a study coordinator may wear the frames with glasses subsystem (such as, wear glasses 310; 600 in FIG. 6; having the HD streaming capability with a camera device embedded within or attached to the glasses or the frame of the subsystem). The study coordinator may then use a first computing device (such as a smartphone having the virtual site monitoring mobile application 313) to communicate to and from the frame and glasses subsystem. The study coordinator may connect a smartphone 313 to a camera either integrated with or connected to the glasses and frame subsystem 310 by a near-field proximity communication, such as Bluetooth®, or even broader range but local communication such as Wi-Fi®. Alternatively, a wired connection may be provided between the glasses and frame subsystem, including the camera, and the smartphone.

The smartphone or other computing device 313 may adapted to store one or more video streams or data from the camera 310, and can further stream any video streams or data to field devices 308 at a CRA's location. The smartphone or other computing device 313 may be used to stream a video stream or data to field devices 308 at a CRA's location using a system 700 described in FIG. 7. During an inspection, a transmitted script from a field device 308 may be displayed with the video stream on a first computing device used by the study coordinator at the inspection site, which may be smartphone 313. Furthermore, the script enables responses from the first computing device 313. The smartphone 313, or other computing device, via its virtual site monitoring mobile application, enables immutable association of two or more of locations, time stamps, the video stream, the responses to the script, or a device identifier.

Such immutable associations may be by marking a file with metadata, tags, or encryption that prevents changes to such information.

Data retrieved from the frame and glasses subsystem 310 may be stored in the smartphone or other computing device 313, along with data captured by the smartphone or other computing device itself. The smartphone or other computing device 313 may transmit this data to a cloud server 315 via an internet 314 connection. A virtual site monitoring application 301 used (such as accessed) on a field device 308 at a CRA's location may include live video streaming 305. Data transmitted from the smartphone or other computing device 313 to the internet 314 (to the cloud server 315) may be also transmitted or accessed from the virtual site monitoring application 301, on the field devices 308 at the CRA's location. Reference numeral 308 is interchangeably used to indicate field device or location and it is understood and made explicit as to which aspect is being discussed in embodiments herein.

The video stream or data may stream in real-time 305 to CRAs and/or other participants as a study coordinator conducts an immutable virtual PSSV using glasses 310; 600 embedded with the camera 310. The virtual site monitoring application 301, which may be executed by the smartphone or other computing device 313 used by the study coordinator, may include a video chat module 304 for video chat sessions between a first and a second computing devices. The video chat session or video session may be an open transmission between the two computing devices. In at least one embodiment, based in part on a video session enabled between the first computing device and the web-based application on the second computing device, an override may be enabled for the script. An override may be enabled by an instruction associated with the video session. In at least one embodiment, an override may be implemented by changes to a form associated with the script. In at least one embodiment, an override may be implemented by persisting a script to continue presenting outside a GPS location identified for the script (or portion thereof).

A CRA or study monitor can transmit text messages (as part of a text chat session) to a study coordinator using the chat module, which may have a text field configured to send data from the field device 308 at the CRA and/or other participants' locations to the smartphone or other computing device 313 via an internet network 314. Such a text chat session or text session may be an open transmission between the two computing devices. Based in part on a video session enabled between the first computing device and the web-based application on the second computing device, an override may be enabled for the script. An override may be enabled by an instruction associated with the text session, and may be implemented by changes to a form associated with the script. For example, an override may be implemented by persisting a script to continue presenting outside a GPS location identified for the script (or portion thereof). In at least one embodiment, a text session or a video session may be part of a session opened by a web-based application.

A CRA can take a screenshot of video stream or data transmitted from smartphone or other computing device 313 to a field device 308 at a CRA's location. Data transmitted from a smartphone or other computing device 313, via an internet network 314, may be transmitted to a website host 316 that may be configured to store said data via a cloud server 315 and its associated database 319. A cloud server 315 may be associated with or may include storage modules 317-319 dedicated to different types of data (video stream, still shots, and clinical trial data).

The virtual site monitoring application 301 may include a file transfer and e-mail module 307, which may be used by a CRA, study coordinator, and/or other participants. The file transfer and email module may allow for any type of electronic communications to be sent and received, such as data files, text files, email, and text messages. The module 307 may be used to upload documents to the virtual site monitoring application 301. For example, data transmitted from a smartphone or other computing device 313 to an internet network 314 (for benefit of a cloud server 315 or a virtual site monitoring application 301) may be transmitted to the cloud server 315 which configured to store said data. Cloud storage can store different aspects of an immutable virtual pre-site study video, including streaming files from the video session 317, camera still shots 318, and a clinical trial database with session folders 319.

The clinical trial database with session folders 319 may include a structured (such as, indexed) collection of data and may be adapted to be managed by any suitable database management systems. The database management systems may be able to define, create, query, organize, update, and manage database(s). And, the database management systems may include one or more of: a MySQL® (Structured Query Language) Database, a PostgreSQL® Database, a Microsoft SQL® Server Database, an Oracle® Database, an SAP® (Systems, Applications, & Products) Database, or an IBM DB2® Database.

Communication between the smartphone or other computing device 313, the glasses 310, the field devices at the CRA's location 308, and/or the one or more databases may be implemented by wired and/or wireless communication therebetween. Therefore, system 300 may include software and/or hardware components configured to implement such wired and/or wireless communication. Further, the wired and/or wireless communication may be implemented using any one or a combination of wired and/or wireless communication network topologies (such as, ring, line, tree, bus, mesh, star, daisy chain, hybrid, etc.). The wired and/or wireless communication may be also implemented using any one or a combination of wired and/or wireless communication protocols (such as, personal area network (PAN) protocol(s), local area network (LAN) protocol(s), wide area network (WAN) protocol(s), cellular network protocol(s), powerline network protocol(s), etc.). Exemplary PAN protocol(s) can comprise Bluetooth, Zigbee, Wireless Universal Serial Bus (USB), Z-Wave, etc.; exemplary LAN and/or WAN protocol(s) can comprise Institute of Electrical and Electronic Engineers (IEEE) 802.3 (also known as Ethernet), IEEE 802.11 (also known as Wi-Fi), etc.; and exemplary wireless cellular network protocol(s) can comprise Global System for Mobile Communications (GSM), General Packet Radio Service (GPRS), Code Division Multiple Access (CDMA), Evolution-Data Optimized (EV-DO), Enhanced Data Rates for GSM Evolution (EDGE), Universal Mobile Telecommunications System (UMTS), Digital Enhanced Cordless Telecommunications (DECT), Digital AMPS (IS-136/Time Division Multiple Access (TDMA)), Integrated Digital Enhanced Network (iDEN), Evolved High-Speed Packet Access (HSPA+), Long-Term Evolution (LTE), WiMAX, etc.

The communication software and/or hardware used may depend on network topologies and/or protocols implemented, and vice versa. Exemplary communication hardware may include wired communication hardware including, for example, one or more data buses, such as universal serial bus(es); and one or more networking cables, such as, coaxial cable(s), optical fiber cable(s), and/or twisted pair cable(s). Further exemplary communication hardware may include wireless communication hardware, such as one or more radio transceivers and one or more infrared transceivers. Additional exemplary communication hardware may include one or more networking components (such as, modulator-demodulator components, gateway components, etc.).

System 300 may also include one or more input devices (such as, one or more keyboards, one or more keypads, one or more pointing devices such as a computer mouse or computer mice, one or more touchscreen displays, microphone, etc.), and/or can comprise one or more display devices (such as, one or more monitors, one or more touch screen displays, projectors, etc.). In at least one embodiment, one or more of the input device(s) can be similar or identical to keyboard 104 and/or a mouse 110 shown in FIG. 1. Further, one or more of a provided display device(s) may be a monitor 106 and/or screen 108.

The input device(s) and a display device(s) may be coupled to a processing module(s) and/or the memory storage module(s) of system 300 in a wired manner and/or a wireless manner, and the coupling can be direct and/or indirect, as well as locally and/or remotely situated components. An indirect input/output component may include a keyboard-video-mouse (KVM) switch that may be coupled to provide input device(s) and to provided display device(s). The coupling may also include a coupling to a processing module(s) and/or a memory storage module(s). The KVM switch also can be part of system 300. In addition, processing module(s) and a memory storage module(s) may be local and/or remote to each other.

Figure 4:
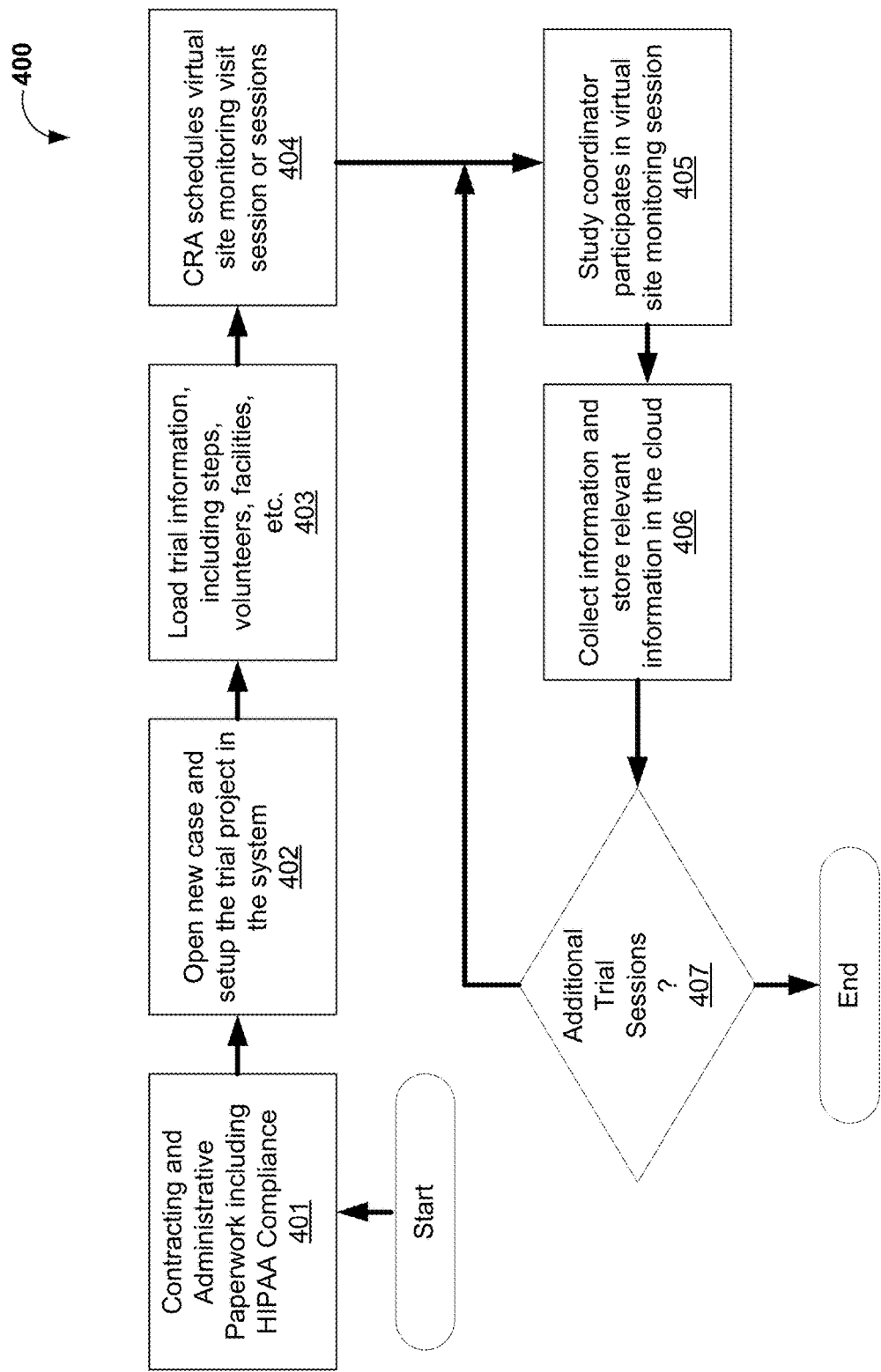
FIG. 4 illustrates aspects of a method for an immutable virtual pre-site study according to at least one embodiment herein.

FIG. 4 illustrates aspects of a method 400 for an immutable virtual pre-site study according to at least one embodiment herein. While this description is provided with respect a pre-site study, the method may also be used to implement other site studies and inspections, including, follow-up inspections, compliance inspections, trial visits and inspections, and trial-end visits and inspections. The method 400 may be implemented on a system 300 or other systems, such as systems previously described and further described in subsequent figures herein, and an order of activities in a method 400 herein may be changed but still results in an immutable virtual pre-site study of the present detailed description. For any particular inspection and study, the steps of method 400 may be performed in any suitable order. In addition, certain of the steps or sub-steps that may be combined or skipped. One or more steps or sub-steps of method 400 may be implemented via computer instructions configured to executed on one or more processing modules that may be at least one processor, such as the processing module(s) described above with respect to computer system 100.

The method 400 may include a step or sub-step (also referred to as an activity) 401 of contracting and storing administrative paperwork including for Health Insurance Portability and Accountability Act (HIPAA) compliance in a virtual site monitoring application system 301 that is associated with at least one field device, such as a second computing device 308 of a CRA's location. The method 400 may include an activity 402 for opening a new session and to setup a session in a virtual site monitoring application 301 and on the smartphone or other computing device 313. The session may also establish the virtual site monitoring application system with cloud storage 317-319 and web host 316.

The method may further include an activity 403 of loading session information data, including necessary equipment information for a clinical research trial. In at least one embodiment, volunteers available for a clinical research trial may be part of such information. Information pertaining to facilities of a clinical research trial may be stored in memory located within the cloud server 315 and/or website server 316. Activity 403 may include a feature for associating a script with an audio stream. This audio stream may be synchronized with a video stream and may be provided to a user (such as a study coordinator) of the first computing device or a user (such as the CRA or other participants) of the second computing device.

Method 400 may include an activity 404, by a CRA, of scheduling a virtual site monitoring session or sessions using a virtual site monitoring application 301. In at least one embodiment, at such a scheduled time, a session may be opened, and participants may request or be allowed to join. In addition, the method may include an activity 405 of starting a pre-trial session, such as by clicking on a button on the virtual PSSV application. In addition, activity 405 may include enabling or allowing a study coordinator to join and participate in a virtual site monitoring session started by a CRA. Alternatively, a study coordinator may start an unscheduled visit. When an unscheduled visit is started, the study coordinator may contact a CRA or other participant, and request that the CRA or other participate create a virtual site monitoring session or sessions for the unscheduled visit. Starting the session, as shown in activity 405, may include the steps described below with respect to FIG. 5.

During the session, the method may collect information and store relevant information for the session via an activity 406. This collection and storage of information may include transmission, via system 300, of locations, time stamps, video stream, responses to a script, and device identifier, to a web-based application from a first computing device. Activity 406 may include immutable storage enabled of such information. Immutable storage may be enabled by storing such information as read-only data in the cloud storage. Immutable storage may be also enabled by encryption, metadata, or distributed ledgers. For example, a distributed ledger enables each piece of data stored to be recorded in a distributed ledger which is updated if any changes are made to the data. Such changes may be rejected when a report is generated, thereby making the data immutable. Relevant parts of such information collected during a session may be stored in a cloud server 315 or a website host 316. The method 400 may also include an activity 407 of conducting additional sessions following the steps described in 401-405. When no more trial sessions are required or desired, the method may end.

Figure 5:
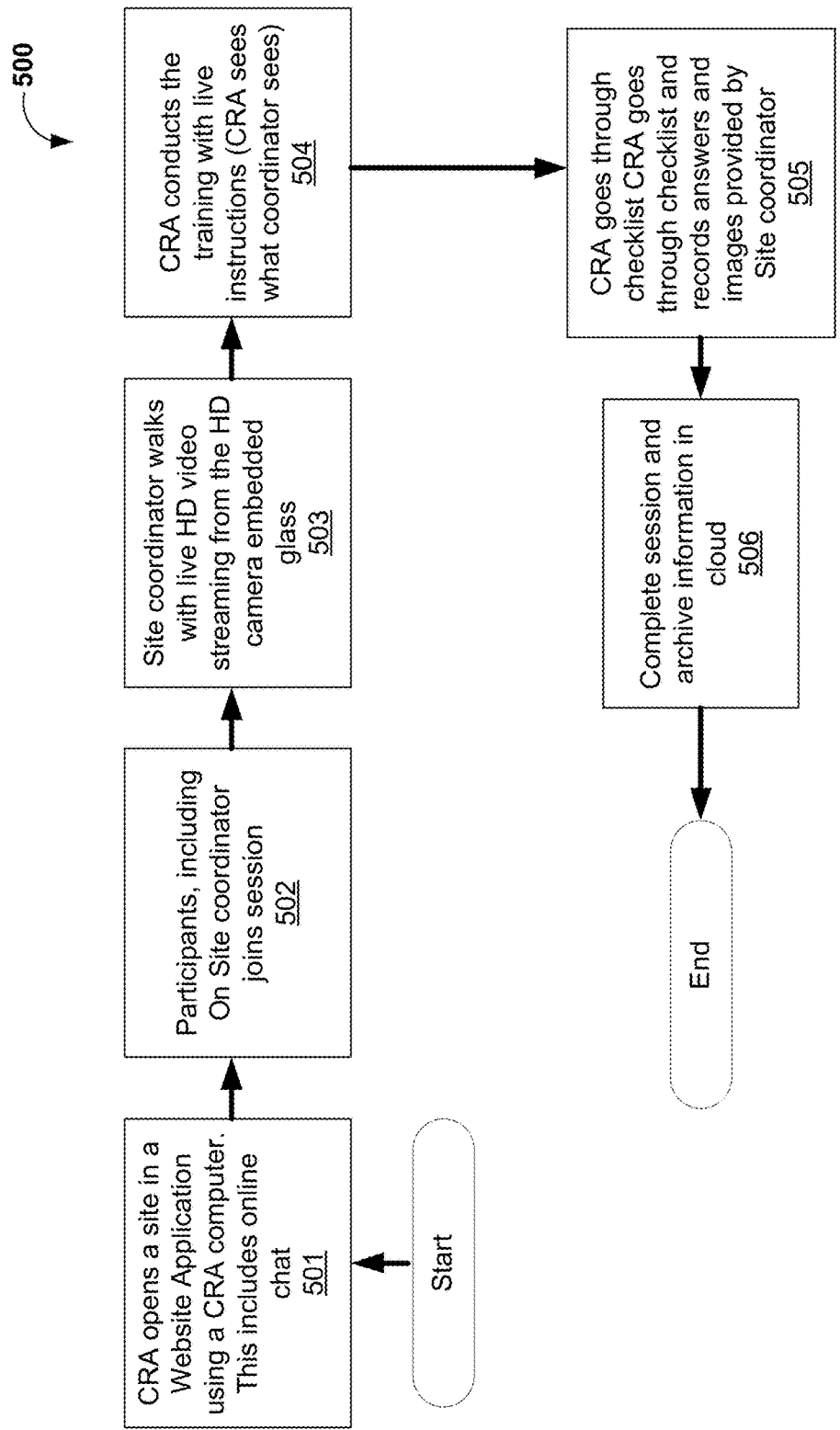
FIG. 5 illustrates other aspects of a method for an immutable virtual pre-site study according to at least one embodiment herein.

FIG. 5 illustrates other aspects of a method 500 for an immutable virtual pre-site study according to at least one embodiment herein. The method 500 may be implemented on a system 300 or other systems, such as systems previously described and further described in subsequent figures herein. The order of activities in method 500 herein may be changed, but still results in an immutable virtual pre-site study of the present detailed description. The method 500 may be performed in any suitable order, and may include steps or sub-steps that may be combined or skipped. One or more steps or sub-steps of a method 500 may be implemented via computer instructions configured to executed on one or more processing modules that may be at least one processor, such as processing module(s) similar or identical to the processing module(s) described above with respect to computer system 100.

The method 500 may include an activity 501 of opening a pre-site study visit session in a virtual site monitoring application 301 using one or more field devices 308 at a CRA's Location. The method may also include an activity 502 of joining a session opened via a virtual site monitoring application. This session may be opened in a cloud computing environment via web host 316 and using cloud server 315. Joining such a session may include associating a first computing device and a second computing device with the session in the cloud computing environment. Joining such a session may also include an activity of controlling entry of third-parties to participate in the session. In at least one embodiment, this may be by receiving requests from such third-parties (such as, from other participants) and approving or denying such requests.

Field devices (such as a second computing device) 308 at a CRA's location may be used to join third-parties to the session. Multiple participants can join a session, including the study coordinator, more CRAs, doctors, and other participants (including clinical research trial participants). The method may include an activity 503 of walking through a research site with live video streaming from an HD camera embedded glasses 310. For example, a site or study coordinator may wear the glasses 100, and walk through the site such that live video and audio are captured by the camera, transmitted to a mobile or computing device, such as a smartphone, used by the coordinator, and then streamed to a field device at the CRA's location. The HD camera may be associated with a frame and glasses subsystem and may be within a lens of the subsystem. Alternatively, the camera may be formed integrally with, embedded in, or attached a frame of the subsystem. As mention, a study coordinator may walk through a research site with live video streaming from such a HD camera.

The method 500 may include an activity 504 of conducting a session by asking questions on the video chat module 304. These questions may come from a CRA or other participates, using the text chat module. In at least one embodiment, such a feature represents an ability of system 500 to incorporate overriding a script by an instruction associated with the video session. In some embodiments, a CRA and/or other participants may also provide questions to override a script. This may be similarly implemented for text chat instead of a video session. In at least one embodiment, a text chat module 307 may be used to implement such feature instead of or together with a video chat module 304.

Figure 13A:
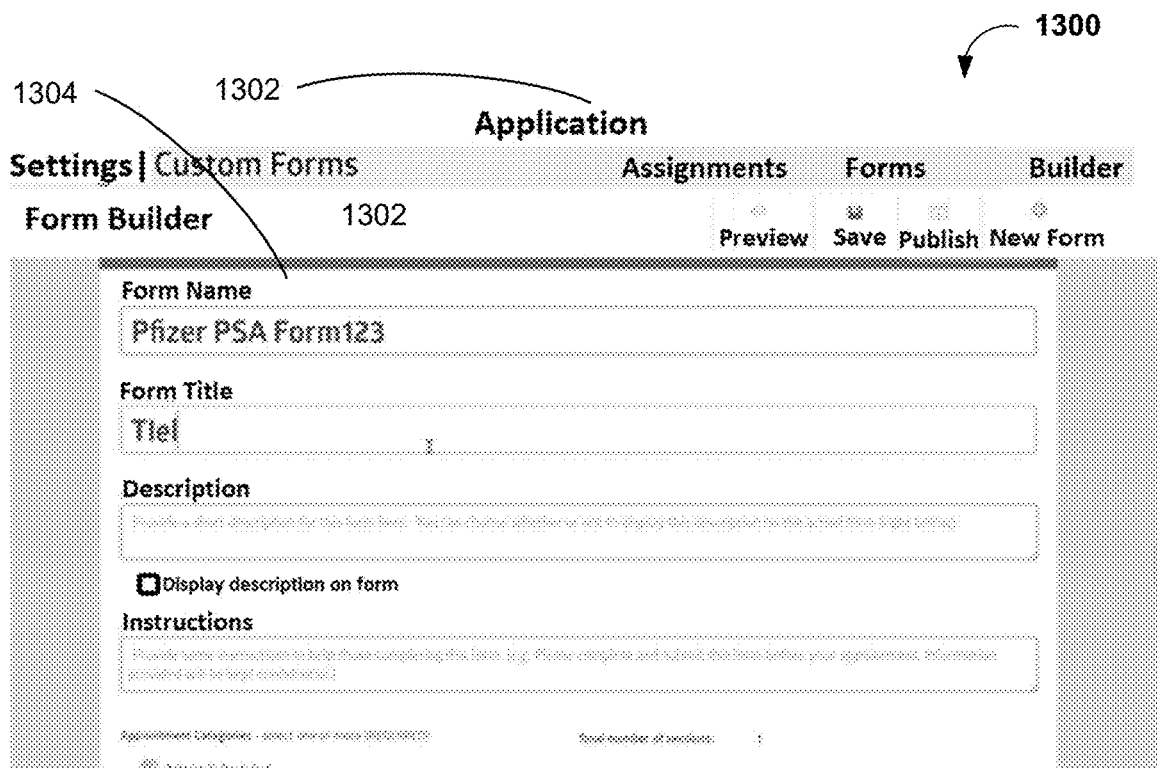
FIGS. 13A, 13B, 13C illustrates a form aspects for a script to be associated with at least a video stream in a system for an immutable virtual pre-site study according to at least one embodiment herein.
Figure 13B:
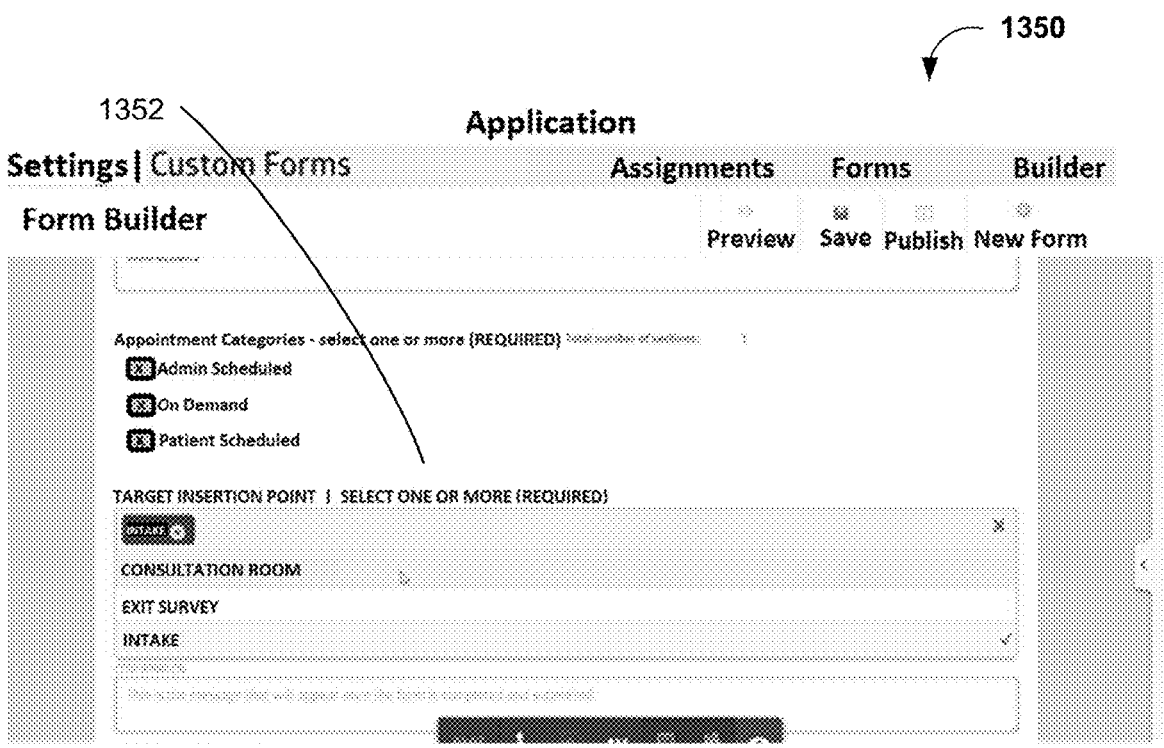
Figure 13C:
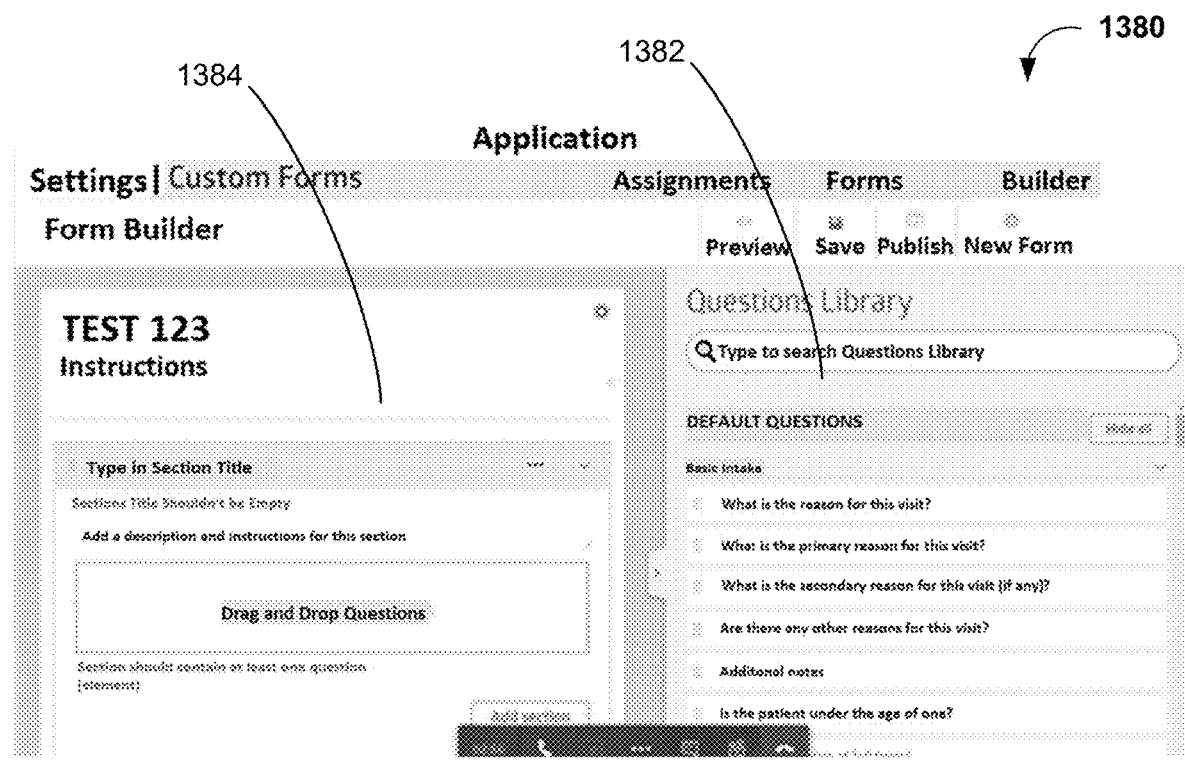

A virtual site monitoring application (web-based application) may be used to populate pre-made questions to a CRA and/or other participants in a script using a form and a form creation application, such as in FIGS. 13A-C. The CRA or other participates may then use this script to ask questions or direct the study coordinate during the session. The questions from a script may automatically synchronize with a video stream based in part on GPS location of a frame and glasses subsystem, and the script may be presented with the video stream based in part on the locations being associated with inspection actions during an immutable virtual pre-site study. For example, certain equipment may be at a specific location for a specific use.

In addition, inspection of such equipment may be tied to an inspection action—such as space and processing capability of a machine. For example, questions may be provided from a script depending on such a location within a research site. Based on image identification of an equipment, questions may be presented from a script. Moreover, a web-based application enables association of the script with the video stream, the timestamps, and the location in an immutable manner, prior to transmission from the first computing device to the web-based application. The questions provided via video or text may be used to override the script and may be provided directly to the study coordinator. CRAs and/or other participants may also create custom questions in a virtual site monitoring application 301 to ask a study coordinator during the session via a script.

The method may also include an activity 505 of reviewing a checklist. This may include enabling a CRA to go through a checklist and to record answers and images provided by a site coordinator using a frame and glasses subsystem associated with a first computing device. A study coordinator may participate in a live question and answer session using a video session module 303 in a virtual site monitoring application 301, and the participation may result in answers and images recorded and associated with a script. The method may also include an activity 506 of completing the session. Activity 506 may include generating a report having the locations, the time stamps, the video stream, the responses to the script, and the device identifier. This report may be provided from the first computing device or from the web-based application on the second computing device to any requesting device or to be stored in the cloud storage 315.

Other information entered into a virtual site monitoring application can be archived into the cloud server 315 and/or website server 316. This information may include, by example, identification, sex, birthdate, age, race, ethnicity, language, visit status, date and time, visit type, class, and method (video or audio) of a session. In at least one embodiment, a smartphone or other computing device 313 may store date, time, and length of time of a session, and may further be associated with GPS features as described with respect to FIG. 3, such that the GPS can provide location information which is also stored.

For example, the smartphone or other computing device 313 may be used to store a location of a research site during a session using a GPS to track such a location. The smartphone or other computing device 313 may transmit data including, by example, location the date, time, length of time, and a location of a research session to a virtual site monitoring application. In at least one embodiment, at an end of a session, such information may be archived into a visit summary that forms a report as also described with respect to at least activity 506. The archived visit summary may be stored in a cloud server and/or a website server.

FIG. 6 illustrates a frame and glasses subsystem 600 for an immutable virtual pre-site study according to at least one embodiment herein. The frame and glasses subsystem 600 includes a frame 601 with respective glasses (or referred to as lenses) 602 and 603. The subsystem 600 may include goggles, glasses (including frames), or any form of optical wearables. The lenses of the glasses fit within channels in the frame 601. The frame 601 has legs 604, which may be pivotally attached to hinges 605. In at least one embodiment, connectivity is provided between legs 604 and glasses 602, 603.

The frame 601 may have a bridge with nose pads 606 formed within or attached to a frame 601. A camera 607 (a video or still camera) may be embedded within provided lens 602 and/or 603. Alternatively, the camera may be mounted on the frame 601 of the glasses, formed integrally with the frame 601, or otherwise connected to the frame 601. The camera 607 may be high definition (HD) camera, which can capture HD video and HD still photographs. The camera comprises may include an image processor 609, a storage device 610, an image buffer 611, and a compression module 612. In addition, the camera may be configured to detect, process, transfer, store, and/or replay video image data between the frame and glasses subsystem and a first computing device (as illustrated in FIG. 7).

Figure 7:
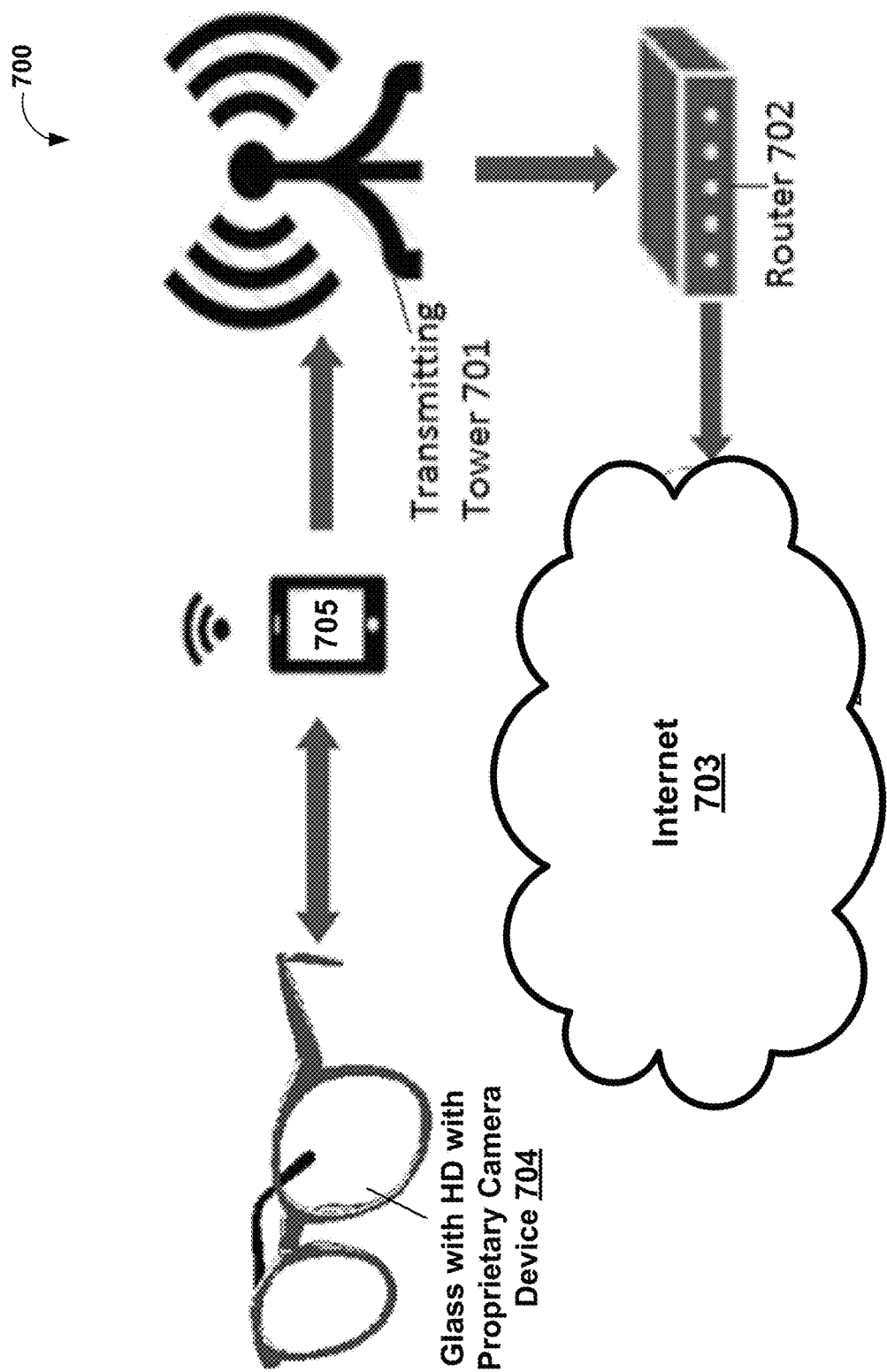
FIG. 7 illustrates a communication aspects in a system for an immutable virtual pre-site study according to at least one embodiment herein.
Figure 8:
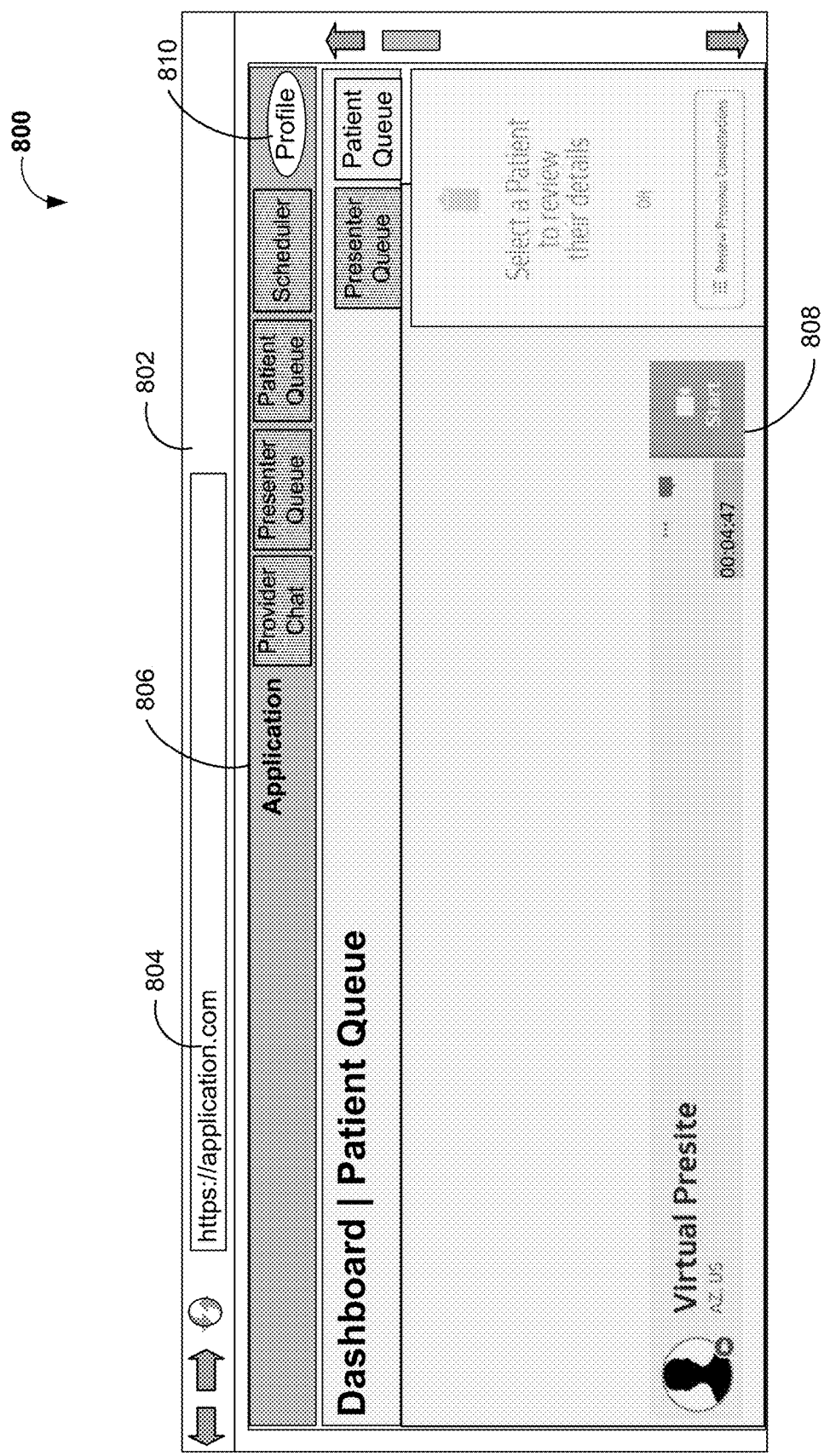
FIGS. 8-12 illustrate user interface aspects for an immutable virtual pre-site study according to at least one embodiment herein.

FIG. 7 illustrates a communication aspects in a system 700 for an immutable virtual pre-site study according to at least one embodiment herein. In particular, FIG. 7 illustrates a system and method in which a mobile phone (such as a smartphone forming the first computing device 705) streams a video stream or data to a CRA/participant(s)' computer. In at least one embodiment, such a smartphone 705 (or 313 in FIG. 3) is able to connect to a camera 310 (607 in FIG. 6) embedded within the glasses 704. The smartphone (such as smartphone 313 of FIG. 3) includes a virtual site monitoring mobile application configured to activate a camera embedded within or associated with the glasses 704.

The smartphone or other computing device 313 may have a GPS device 311 (which may be an integrated GPS device) to track location of a frame and glasses subsystem or a smartphone, which then facilities wireless communication to computing devices outside a research site. An image processor 609 within the camera may be able to retrieve image data, and the camera may be able to transmit video stream or data to a smartphone 705. Then, the smartphone 705 may be able to transmit packets of a video stream or of video data to cell phone towers 701 via radio waves. For example, video stream or data may be transmitted from a cell phone tower 701 to a router 702. The router 702 directs each packet to an internet type of network 703, and the network 703 may be able to transmit data to a virtual site monitoring application 301 stored on or accessible to a field device 308 at a CRA and/or other participants' locations.

FIGS. 8-12 illustrate user interface aspects 800-1200 for an immutable virtual pre-site study according to at least one embodiment herein. In at least one embodiment, an application 806 includes scheduled and on-demand appointments listed, along with an option 808 to start or open a session. The application 806 may be accessible as a web-based application within a browser 802 via a website link 804. Alternatively, the application 806 may be accessible via a standalone web application, or may be provided as an application running on a mobile device. The sessions started or opened, including based on scheduled or on-demand appointments, may be associated with the immutable virtual pre-site study where a study coordinator is located at a research site. During the session, a first computing device at a research site is linked to the session, and an immutable virtual pre-site study may be performed using the first computing device that is linked to the session and that is associated with a frame and glasses subsystem.

Figure 9:
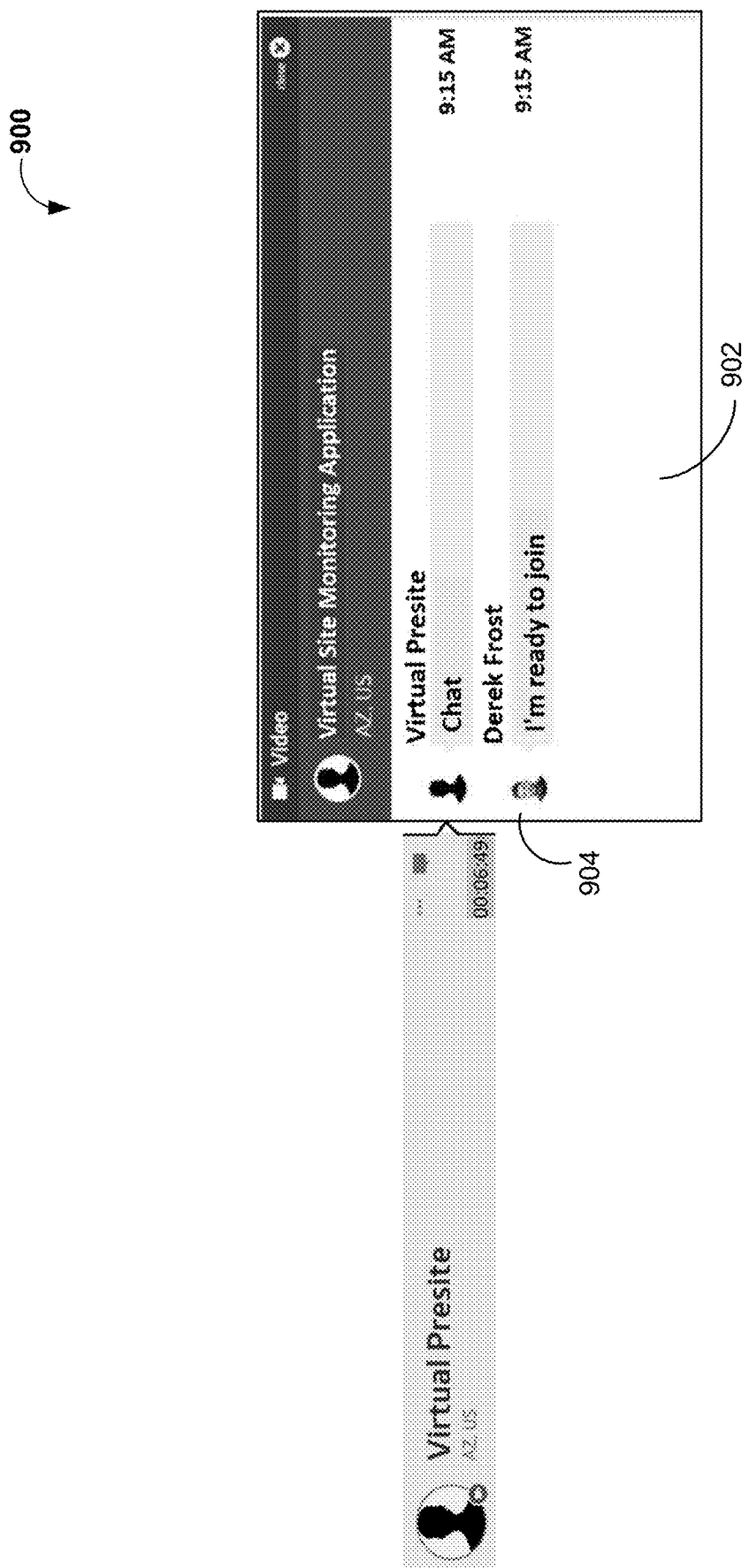

FIG. 9 illustrates user interface aspects 900 after a session option 808 is selected. A research site's study coordinator may be represented by a first listing in a session section 902, and CRAs 904 may be subsequently listed. Selecting a listing in session section 902 allows denial of permission to a third-party participant in a session. As shown in FIG. 9, the interface may present a chat interface for a study coordinator and CRA or other participant to communicate and join a session.

Figure 10:
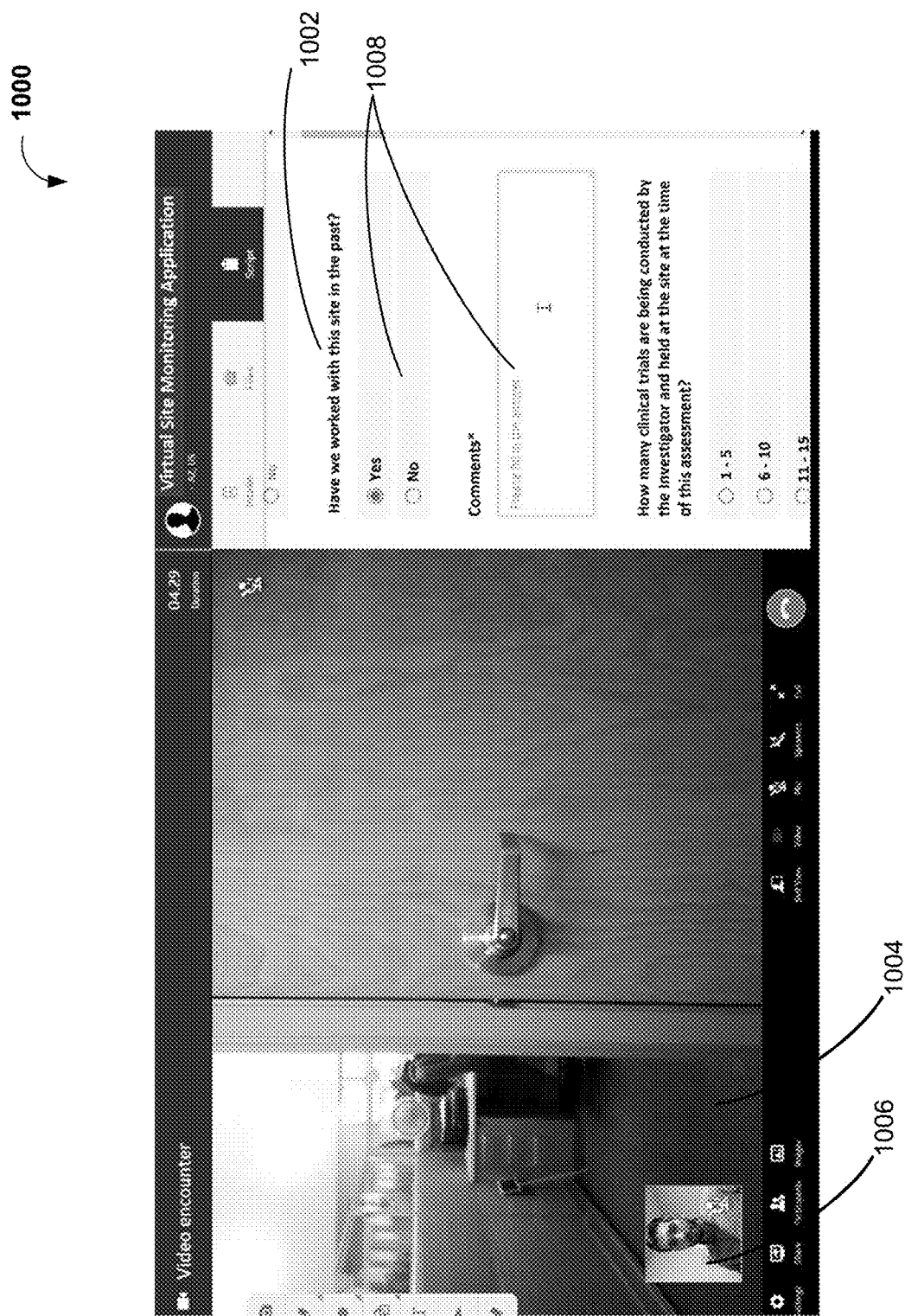

FIG. 10 illustrates a user interface (UI) 1000 of the virtual site application having a video stream 1004 that has a coordinated or synchronized portion 1002 of a script within an application. The user interface 1000 also includes a section video of a CRA monitoring actions of a study coordinator. The script may be transmitted from a web-based application of a CRA (on a second computing device) to a first computing device located at a research site, with the second computing device being remote from the first computing device. The script (or portion 1002 thereof) may be associated with a video stream 1004 from a camera of a frame and glasses subsystem and with a location determined by a GPS for the frame and glasses subsystem. The UI 1000 also illustrates responses 1008 enabled by the script 1002.

Figure 11:
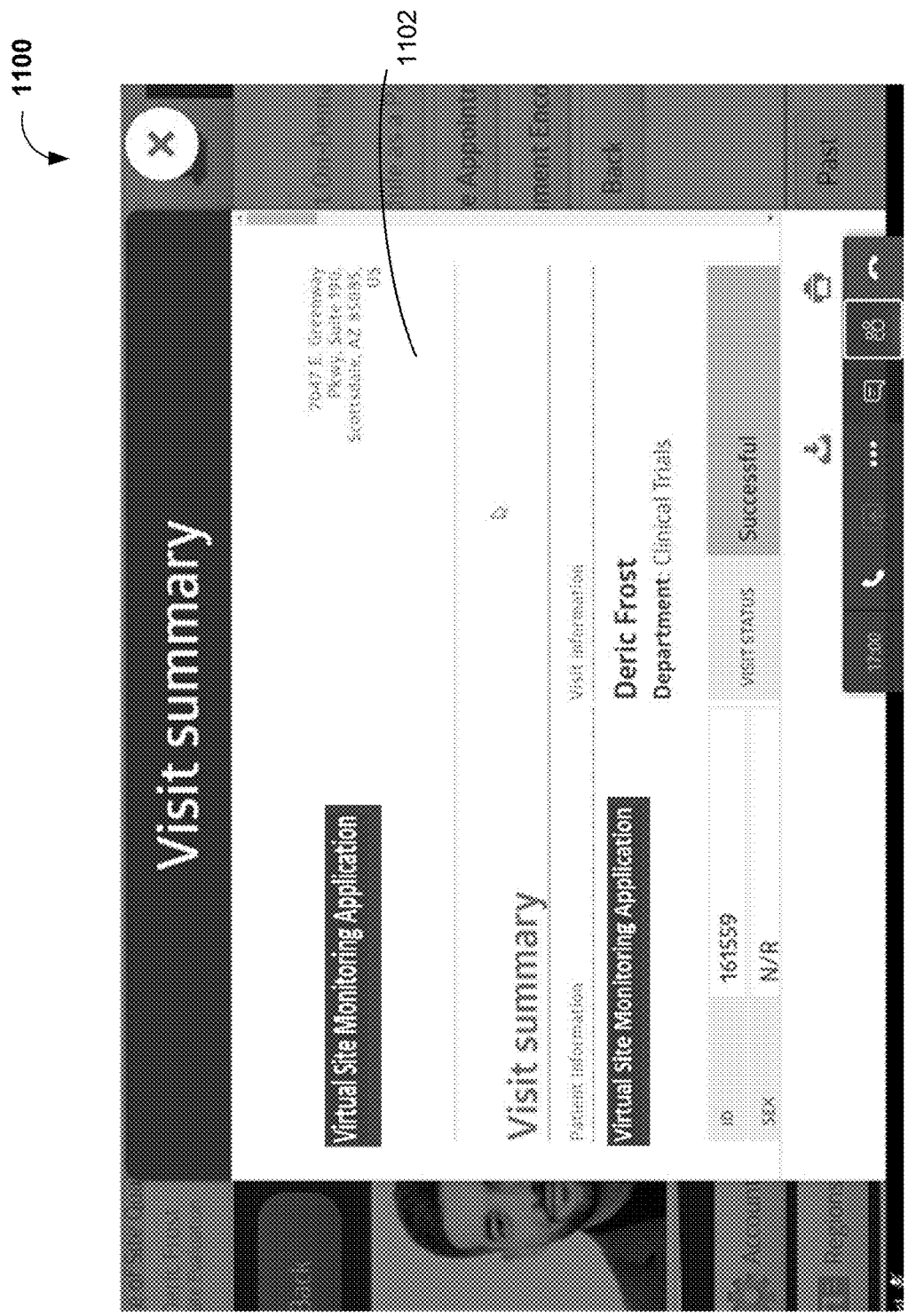
Figure 12:
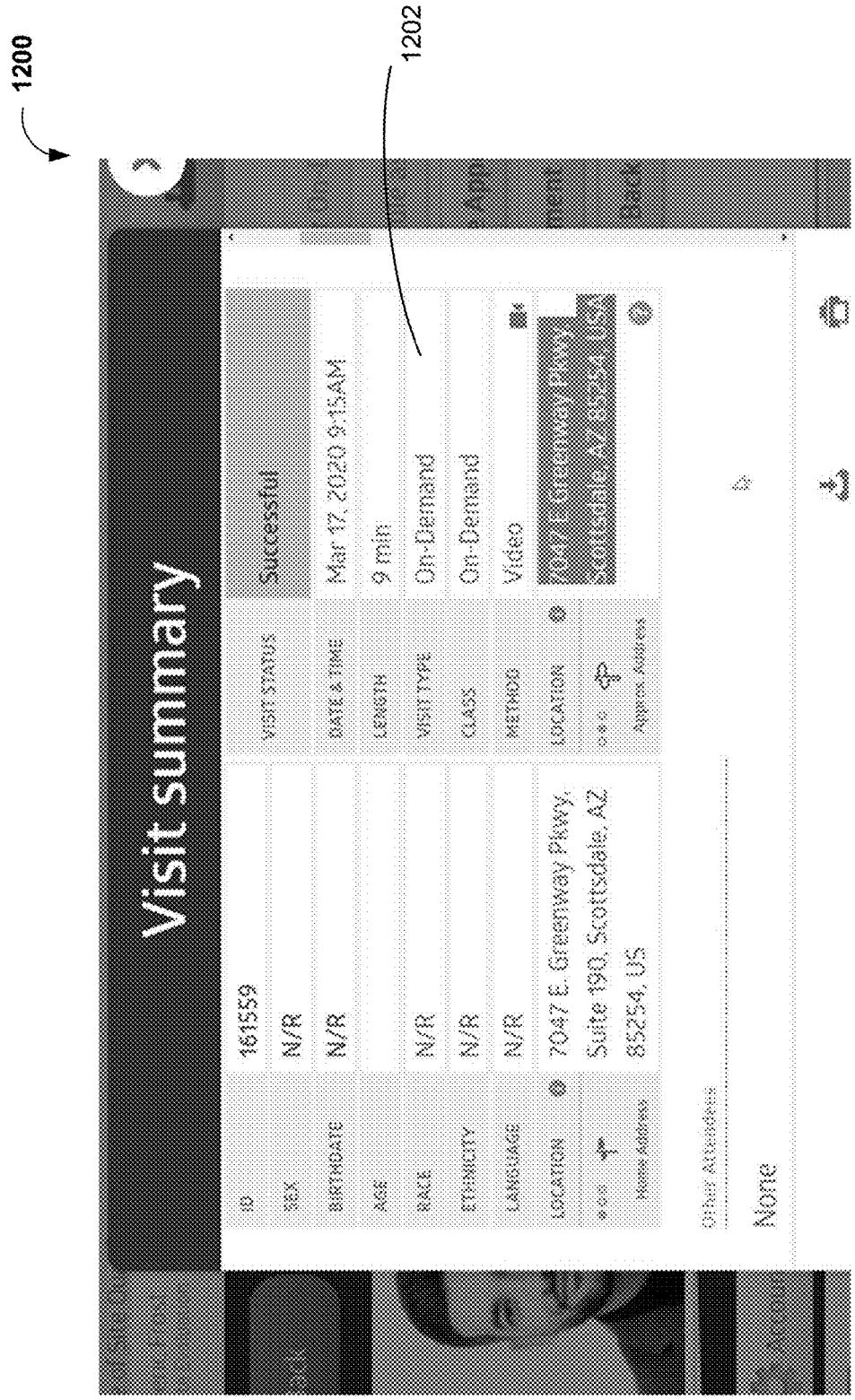

FIGS. 11 and 12 illustrate user interface (UI) aspects 1100, 1200 of an application on a first computing device or a second computing device. Upon completion of an immutable virtual PSSV, the application is able to generate a report or a visit summary which may include information 1102, 1202 gathered during the an immutable virtual PSSV the locations, the time stamps, the video stream, the responses to the script, and the device identifier. The device identifier may include an identifier (such as an internet protocol address or a media access control address of one or more of a frame and glasses subsystem or a first computing device). In at least one embodiment, such a report may be provided from the first computing device or from the web-based application on the second computing device.

A study monitor (such as at a CRA location) may be able to manage site status via information provided to a CRA and for entry in the site profile 810 during planning of an immutable virtual PSSV. The site profile may be made available for editing on the immutable virtual site monitoring mobile application, where such information and any changes may then be passed to the web-based application. Site statuses may include pre-qualified, qualified, not qualified, active, closed, and locked. In addition, the UI of the web-based application or the mobile application may be adapted to perform certain functions. For example, when a study monitor adds a site to a study, a system (such as system 300) sets a site status to pre-qualified. As such, all sites begin with this status when they enter the web-based application (for the CRA).

In the UI of FIGS. 8-12, a site status dropdown may always displays a current status of a site when collapsed. Further, when the dropdown is open the current status appears at the top of a list of statuses with a checkmark next to it. When a study monitor changes a site status, the system presents an alert to confirm the intention. To complete the site status change, a study monitor must type or select a word, icon, or selectable option as confirmation they intend to make the change. For example, when the site status is pre-qualified, the additional statuses available in the site status dropdown will only include qualified or not qualified. The study monitor would then be limited to selecting from these limited options.

When the site status is qualified, the additional statuses available in the site status dropdown will be pre-qualified, not qualified, active, and locked. Further, when the site status is active, the additional status available in the site status dropdown is closed. When the site status is closed, the only additional status available in the site status dropdown is: locked. Further, when the site status is locked, the site status dropdown displays this status, but the dropdown may be in a disabled state. The site status then cannot be modified.

When a study monitor attempts to change the site status and when there are scheduled visits for the visit types associated with that site status, the application may alert the study monitor that they must cancel or complete all scheduled visits before changing the site status. When the study monitor attempts to change the site status, but there are incomplete or unresolved visits for the visit types associated with that site status, the system alerts the study monitor that they must complete or resolve all pending visits before changing the site status.

There may be two user account types for the application 301 executing on at least one computing device of a system 300, such as in a cloud server 315, a website host 316. A first account is for a study coordinator and a second account is for a study monitor. As described herein, a study coordinator may act as the "eyes" for the study monitor to see a site during a site visit. The study monitor can manage large studies with many sites throughout the lifecycle of a study. As such, there may be multiple sessions maintained distinctly and immutable from each other.

When a new site seeks qualification for a study, the study monitor can create a new site profile using UI aspects 800 and can begin a qualification workflow. Study monitors can invite site staff (such as, study coordinators) to create an account in association with the qualification workflow. Study coordinators may then activate their account in preparation for an immutable virtual PSSV. When a study monitor has multiple sites seeking qualification, the study monitor may manage the research sites by maintaining a status for each research site in a study. In addition, the provided UI aspects 800 also support other types of visits, such as a training visit, a compliance visit, and trial-end visit.

Research sites may also enter a study with a status of pre-qualified. Then, using immutable virtual site monitoring visits (presenting immutable virtual an immutable virtual PSSVs) by the present system and method, evaluation may occur for the site throughout the lifecycle of the trial. The site status may need changing based in part on how the research site functions as part of the study—as covered elsewhere throughout this detailed description. A study monitor can conduct a variety of different types of research site visits (an immutable virtual PSSVs) depending on a research site's status. A research site may be subject to a default visit type, such as a site selection, a site initiation, interim monitoring, and closeout.

To begin inspection and evaluation of a research cite, a study monitor may schedule research site visits (an immutable virtual PSSVs) using a scheduler, as illustrated in Application UI 806. A study monitor may then monitor and maintain an inventory of qualified sites for a study that can be activated based on needs of such a study. In at least one embodiment, a study monitor coordinates with research site staff using a variety of communication methods enabled by UI aspects 800, 900. Such UI aspects included chat, video calls, and audio calls.

For a research site visit, a study monitor tours such a research site virtually using video streamed (feed or broadcast) from a frame and glasses subsystem having at least eyewear (or glasses) worn by a study coordinator who may be a research site staff. All research site visits may have a defined visit type that is associated with a site's status, as noted elsewhere in this detailed description.

For example, research sites with a status of pre-qualified may have one or more site selection visits. Separately, research sites with a status of active, may have one or more interim monitoring visits. Visit types may be customizable on a study-by-study basis and may be associated with any site status. A study coordinator may be able to toggle between a camera of a frames and glasses subsystem and that of a first computing device (such as a mobile device) at the request of a study monitor via a second computing device interfacing on a web-based application.

A study monitor may be able to view closeups and take snapshots of what a study coordinator sees. A study monitor may be able to then annotate directly on such snapshots or closeups to document a research site's capabilities. Furthermore, screen sharing may be provided for both, a study monitor and a study coordinator to facilitate an immutable virtual an immutable virtual PSSV and to conduct training sessions. In terms of a functional overview of the UI aspects 800-1200, during a research site initiation, at least a study coordinator and a study monitor may use text-based messaging (such as a text chat session) within a waiting room and/or an encounter room. Such text-based messaging may be to communicate as a supplemental option to audio and video communication (via at least a video chat session or a separate audio chat session). These sessions may be part of a session opened via a web-based application of a second computer device at a CRA's location.

In at least one embodiment, a study monitor may open a session via a web-based application and can invite guests to join research site visits and request assistance with any research site visit. During a live visit, a study coordinator can join a video stream using either a web-based mobile application that may also be a regular application associated with a web-based application of a second computing device. A study coordinator may also switch devices (such as using multiple first computing devices at a research site) at any time during a visit to respond to requests from a study monitor. The different devices may be all pre-authorized into a session opened by a web-based application so that there is a smooth transition between such different first computing devices.

A study monitor may also have the ability to dismiss participants from a session individually or collectively. For example, a study monitor can end a session, including a call that is a live video/audio communication with a first computing device at a research site. While this feature may close a session, such closure may be temporary and does not complete an immutable virtual PSSV. Such a feature may, however, dismiss site and guest participants for a determined time period. A study monitor may remain in an encounter room to complete their notes (such as, in preparation for a summary or report 1102, 1202 within a web-based application) before marking a visit as successful and completed. Alternately, a study monitor may mark a visit as incomplete and complete their notes at a different time and in a different location removed from a location of an inspection action or the research site, entirely, as it may be convenient for the study monitor.

When a technical issue occurs in any of the features of a system (such as a system 300 in FIG. 3), a study monitor can also mark a visit as unresolved so that a visit status for the visit may be addressed at a later time. In at least one embodiment, a visit queue may be enabled as illustrated in the UI aspects 800 of FIG. 8. During one or more immutable virtual PSSVs, a study monitor may review a list of study coordinators that have started their visits. For example, a study monitor may be able to determine by a status indicator that such study coordinators are waiting for a session to be opened to begin such one or more immutable virtual PSSVs. A study monitor can review details about a research site and may be able prepare for each of the one or more immutable virtual PSSVs before a walk-through actually begins.

A study monitor may also engage a study coordinator using text-based messaging before beginning an immutable virtual PSSV. For example, a study monitor may be able to flag a site card in a queue with a customizable scheme to prioritize one or more immutable virtual PSSVs waiting in a queue, such as illustrated in the UI aspects 800 of FIG. 8. A study monitor can also send a notification to other study monitors about a specific research site waiting in a queue, if a study is busy and a different study monitor may be able to open a session to conduct an immutable virtual PSSV. In the system, a status for sessions are viewable across a web-based application that is accessible on multiple second computing devices of multiple CRAs or study monitors.

FIGS. 13A, 13B, 13C illustrate form aspects 1300, 1350, 1380 for a script to be associated with at least a video stream in a system for an immutable virtual pre-site study according to at least one embodiment herein. As shown in FIG. 13A, a form application 1302 is presented that may be part of an application 301 in FIG. 3, but may alternatively be an independent application. The form application 1302 may result in an underlying script generated to a format of a UI—as illustrated in FIGS. 8-12. As shown, form application 1302 may include fields 1304 to describe a nature of an immutable virtual PSSV.

As shown in FIG. 13B, form aspects 1350 illustrates where target insertion points 1352 may be defined for indicating where pertinent questions of a script should be coincided with a video stream. For example, when a video stream is at a consultation room, such as determined based on GPS coordinates, questions described in the form for such a target insertion point may be displayed and may enable responses from a study coordinator. As shown in FIG. 13C, form aspects 1380 include selectable options for adding questions or instructions. Questions 1382 may be provided from a library of default or previously stored questions for the script, or may be generated by a user and provided in form section 384. A script may be generated by application 1300 from the questions. The script may have different sections, each associated with a target insertion point. A target insertion point may be converted to an identifier to be matched with an input or with GPS coordinates as a study coordinator inspects a research site using a frame and glasses subsystem and its associated first computing device.

In addition, configurable forms may be a basis for a script generated for a first computing device. For example, an intake form for a study coordinator may be customized within a web-based application 301 or in a separate form application 1302. In at least one embodiment, such a form may be completed upon starting an immutable virtual PSSV or will be turn off for the intake flow. In at least one embodiment, such a form may be customized so that a notes form may be displayed in an encounter room of a research site and so that responses may be provided by a study monitor to complete during an immutable virtual PSSV without a specific question (or using an open question).

A survey may be displayed at an end of an application in a UI aspect to get feedback from a study coordinator and to better understand and assess how an immutable virtual PSSV is performing (or can be improved). All configurable forms may include a variety of standard controls used in web-based forms, including for a decimal number field, an integer field, and a dropdown (single-select) option.

In addition, the form application may include a dropdown (multi-select) option, date, radio buttons, text field (multi-line input), text field (single-line input), legal form (requesting to acknowledge and accept legal disclaimers, for instance), and a file upload option. In at least one embodiment, all configurable forms may have one or more sections and can begin with an instructions view and end with a confirmation view.

All configurable forms may be able to display a set of follow-up questions based on response to a parent question, such as through a script having the follow-up questions and the parent questions at a target insertion point. File sharing may be an optional feature enabled in a UI aspect of the web-based application and the mobile application, to allow allows research sites to securely share files with a study monitor and vice versa (with a study coordinator). As part of this file sharing, a study coordinators can upload a variety of different file types, including PDFs and images, directly before or after an immutable virtual PSSV.

A study coordinator can access file sharing using either the web-based mobile application or a variation of the web-based application, which may be pre-installed on a first computing device shipped to a research site within a research site kit. A visit summary or report 1102, 1202 (such as in FIGS. 11 and 12) may be provided when an immutable virtual PSSV is completed. In at least one embodiment, all immutable virtual PSSVs produce a visit summary or report to document actions and results at such immutable virtual PSSVs. The summary or report is useful for the study monitor to use as part of their assessment of a research site, and may be available from the web-based application as a download in a PDF (or other format) and for printing. To ensure the integrity of the reports is not compromised, these formats may be immutable formats that do not allow for changes. The summary or report may include names of people that participated in an immutable virtual PSSV, such as a study coordinator, a study monitor, and associated guests.

A visit summary or report may include at least a name of a research site where an immutable virtual PSSV was conducted, and can include a date and time of when an immutable virtual PSSV was conducted, as well as the duration of the immutable virtual PSSV. A visit summary or report may also include a type of an immutable virtual PSSV, such as site selection, and whether such an immutable virtual PSSV was a scheduled or on-demand visit.

A visit summary or report may include a visit status, such as that an immutable virtual PSSV was successful, which may be useful for site qualification. Alternately, an immutable virtual PSSV with a status of site did not attend may indicate one or more additional visits may be necessary. In at least one embodiment, when a visit type of an immutable virtual PSSV has a configurable form associated with it, a visit summary or report displays questions and responses received. A study monitor may add to the responses and the additional response may be immutably tied to the summary or report.

When a study monitor captures snapshots during a an immutable virtual PSSV, a summary or report may include those snapshots. When a study monitor chats with a study coordinator in a waiting room or an encounter room at a research site, a visit summary or report includes a transcript of such entire chat.

A visit summary may include any files that were uploaded during an immutable virtual PSSV. For purposes of capacity planning, a scheduler application may be used, and a study monitor can set their availability for specific appointment blocks for scheduled visits and to make themselves available for on-demand visits with research sites requesting for the same.

Study monitors can also set the availability for a team of study monitors and can also schedule site visits on their behalf. In addition, staff chats, such as provided via a text (or video/audio) chat session may be a communication tool that allows a study monitor to quickly connect with other study monitors managing other parts of a study via chat, voice, or video. In at least one embodiment, study monitors may contact research site staff at any research site in a study via such chat sessions without any formality of conducting an immutable virtual PSSV.

In at least one embodiment, the system 300 includes notifications to notify users of important system events via electronic communications, such as short messaging service (SMS) and electronic mail (email). All notifications for a study may be enabled by default. Certain email notifications drive key workflows in a study and cannot be turned off. In at least one embodiment, such notifications include: account activation email, forgot password email, and the guest invite email that brings guests into a session for an immutable virtual PSSV. Other email and electronic communication notifications may be turned off for aspects of a system 300 for an immutable virtual PSSV. Such notifications may include new appointment confirmations, appointment updates, cancelled appointment alerts, upcoming visit alerts, and the addition of new files. In at least one embodiment, appointment notifications may be configured to also alert users via SMS.

A language throughout UI aspects 800-1200, discussed herein may be customized, including in text messages of various session to suit client needs. These language options may also be available to the summary and reports. A lead study monitor may be able to track progress of site activity and status across study monitoring teams using filtering capabilities on a study platform dashboard. In at least one embodiment, reports may be generated to present analytics relevant to a study at the client's request. Bulk data may be also provided to enable import or export of large numbers of records into or out of a system 300 at a client's request while a study is ongoing. A study monitor and a study coordinator may choose from a list of supported languages for an immutable virtual PSSV to be conducted in a specific language that can then cause entire UI aspects, including sessions, in both the web-based application and a mobile application to have the same language.

Figure 14:
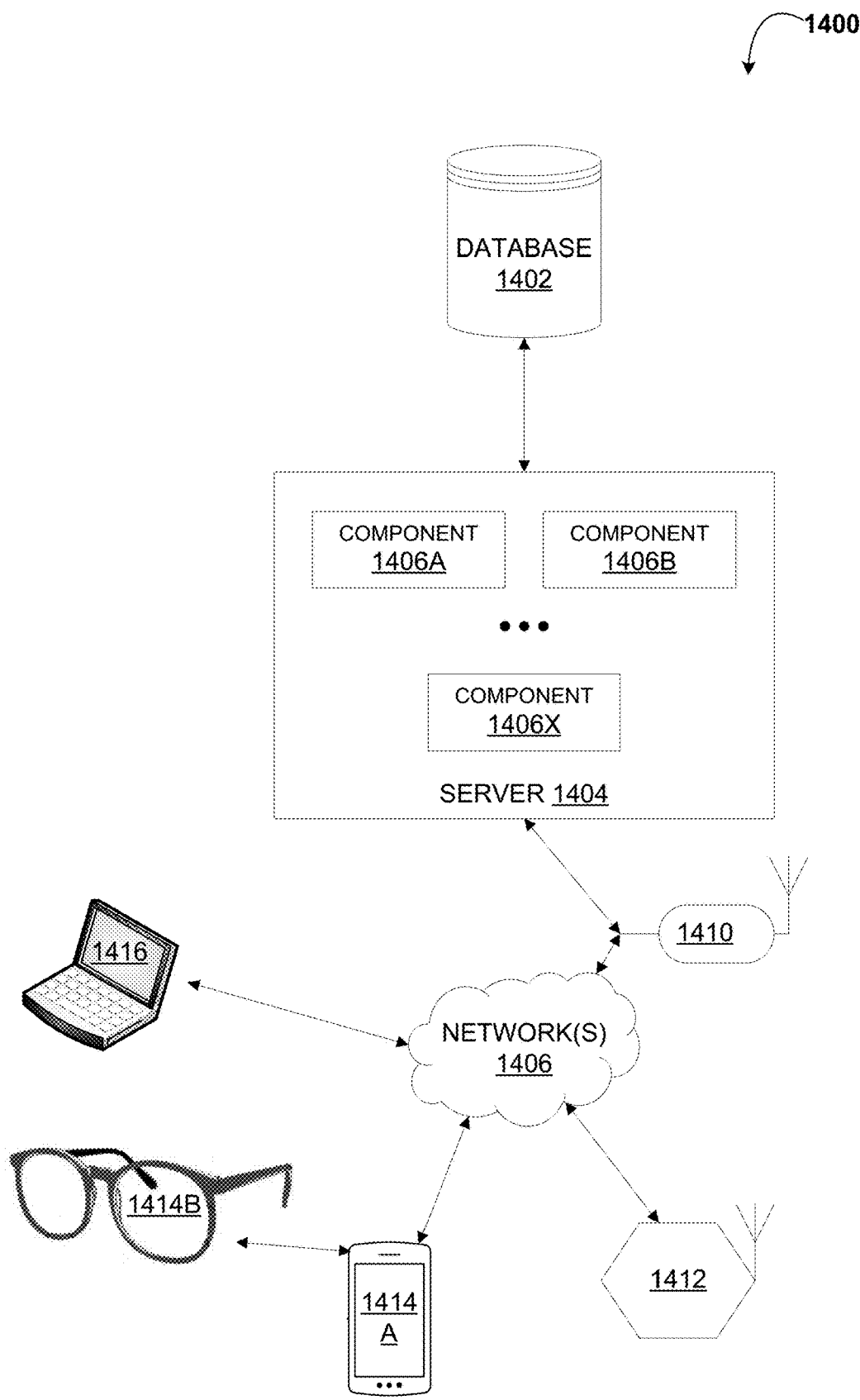
FIG. 14 illustrates a hardware aspects in a system for an immutable virtual pre-site study according to at least one embodiment herein.

FIG. 14 illustrates a hardware (such as computer and network aspects) aspects 1400 in a system for an immutable virtual pre-site study according to at least one embodiment herein. In at least one embodiment, such hardware aspects 1400 may be mapped to a system 300 of FIG. 3. The computer and network aspects 1400 may include a distributed system. In at least one embodiment, a distributed system 1400 may include one or more computing devices 1412-1416. One or more computing devices 1412-1416 may be adapted to execute and function with a client application, such as with browsers or a stand-alone application, and are adapted to execute and function over one or more network(s) 1406.

A server 1404, having components 1406A-X may be communicatively coupled with computing devices 1412-1416 via network 1406 and via a receiver device 1410; 1412, if provided. Components 1406A-X include processors, memory, and random-access memory (RAM). Server 1404 may be adapted to operate services or applications to manage functions and sessions associated with database access 1402 and associated with computing devices 1412-1416. Server 1404 may also be associated with a first computing device 1414A and directly or indirectly with a frame and glasses subsystem 1414B. For example, server 1404 may be part of a cloud computing environment. In at least one embodiment, a second computing device 1416 executes a web-based application to communicate with a first computing device 1414A. As such, these computing devices 1416 and 1414A are at distinct locations from each other.

One or more computing devices may be adapted to transmit, either through wired or wireless communication channels, information received therein, including dosage information and results from a spectrometer or detector. This information may be received in a receiver device and transmitted to a monitor device that infers from changes in electrical properties based in part on instructions stored therein. The server 1404 may include components to function as a web host distinctly from a cloud computing environment. In at least one embodiment, one or more components 1406A-X may be adapted to function within a server 1404 for performing functions discussed with respect to a first computing device 308 and with respect to a smartphone or other computing device 313 of FIG. 3, and that are associated with a cloud server 315. In at least one embodiment, one or more components 1406A-X and 1416 may include one or more processors and one or more memory devices adapted to function as a monitor device, while other processors and memory devices in server 1404 may perform other functions.

Server 1404 may also provide services or applications that are software-based in a virtual or a physical environment. When server 1404 is a virtual environment, then components 1406A-X are software components that may be implemented on a cloud to allow remote operation of certain computing devices, as discussed at least in reference to FIG. 3. This also allows for remote access to information received and communicated between any of aforementioned devices. One or more components 1406A-X of a server 1404 may also be implemented in hardware or firmware, other than a software implementation described throughout herein. In at least one embodiment, combinations thereof may also be used.

One computing device 1416 may have at least a microcontroller and memory having instructions to enable display of information received from a first computing device 1414A. Another computing device 1412 may be a transmitter device to transmit directly to a receiver device 1410 or to transmit via a network 1406 to a receiver device 1410 and to a server 1404, as well as to other computing devices 1414. The other computing devices 1414 may include portable handheld devices that are not limited to smartphones, cellular telephones, tablet computers, personal digital assistants (PDAs), and wearable devices (head mounted displays, watches, etc.).

The other computing devices 1414 may support applications designed as internet-related applications, electronic mail (email), short or multimedia message service (SMS or MMS) applications and may use other communication protocols. The other computing devices 1414 may also include personal computers and/or laptop computers running one or more operating systems discussed elsewhere in this detailed description. Thin-client devices, including gaming systems (Microsoft Xbox®) may be used as other computing device 1414. Moreover, network(s) 1406 may be any type of network that can support data communications using various protocols. These networks 1406 may be networks that are based on Ethernet, Token-Ring, a wide-area network, Internet, a virtual network, a virtual private network (VPN), a local area network (LAN), an intranet, an extranet, a public switched telephone network (PSTN), an infra-red network, a wireless network (such as that operating with guidelines from an institution like the Institute of Electrical and Electronics (IEEE) 1402.11 suite of protocols, Bluetooth®, and/or any other wireless protocol), and/or any combination of these and/or other networks.

The server 1404 may run a suitable operating system, including any of operating systems described throughout herein. The server 1404 may also run some server applications, including HTTP (hypertext transport protocol) servers, FTP (file transfer protocol) servers, CGI (common gateway interface) servers, JAVA® servers, database servers, and/or variations thereof. A database 1402 may be supported by database server feature of a server 1404 provided with front-end capabilities, and the database 1402 enables immutable information storage of information received from a first computing device. In at least one embodiment, such database server features include those available from Oracle®, Microsoft®, Sybase®, IBM® (International Business Machines), and/or variations thereof.

As such, a system for immutable virtual pre-site study may include a frame and glasses subsystem that has glasses and/or goggles, and at least one processor for executing instruction from memory of the system. The subsystem may include a frame, one or more legs pivotally attached to the frame, one or more detachable lenses coupled to the frame and a camera embedded within or associated with one or more lens of the subsystem. Further, the system includes an image processor, a storage device, a compression module, an image buffer, an image sensor, and a smartphone. Such a smartphone includes a mobile application that is adapted to activate a camera of the subsystem.

In at least one embodiment, a computing device has a virtual site monitoring application, one or more processing modules, and one or more non-transitory storage modules storing computing instructions configured to run on (or execute on) the one or more processing modules, which causes the one or more processing modules to perform activities discussed with respect to at least FIGS. 4 and 5. These activities include opening a session on the application, joining a session on the application, accessing a mobile application that is adapted to activate a camera a subsystem, enabling camera access and microphone access on the application and the smartphone mobile application, transmitting a video stream or data from the camera to smartphone, and transmitting the video stream or data from the smartphone to a computing device that has the application and that is remote from the smartphone.

Aspects of system 1400 may be sent from a CRA's location to a research site in preparation for an immutable virtual PSSV. For example, eyewear with an embedded HD camera 1414B and a smartphone 1414A (such as an Android® mobile device with the mobile application pre-installed) may be sent to the an immutable virtual PSSV to be used by a designated study coordinator. Further accompaniments, such as customized packaging, and site visit training materials may also be included.

Figure 15:
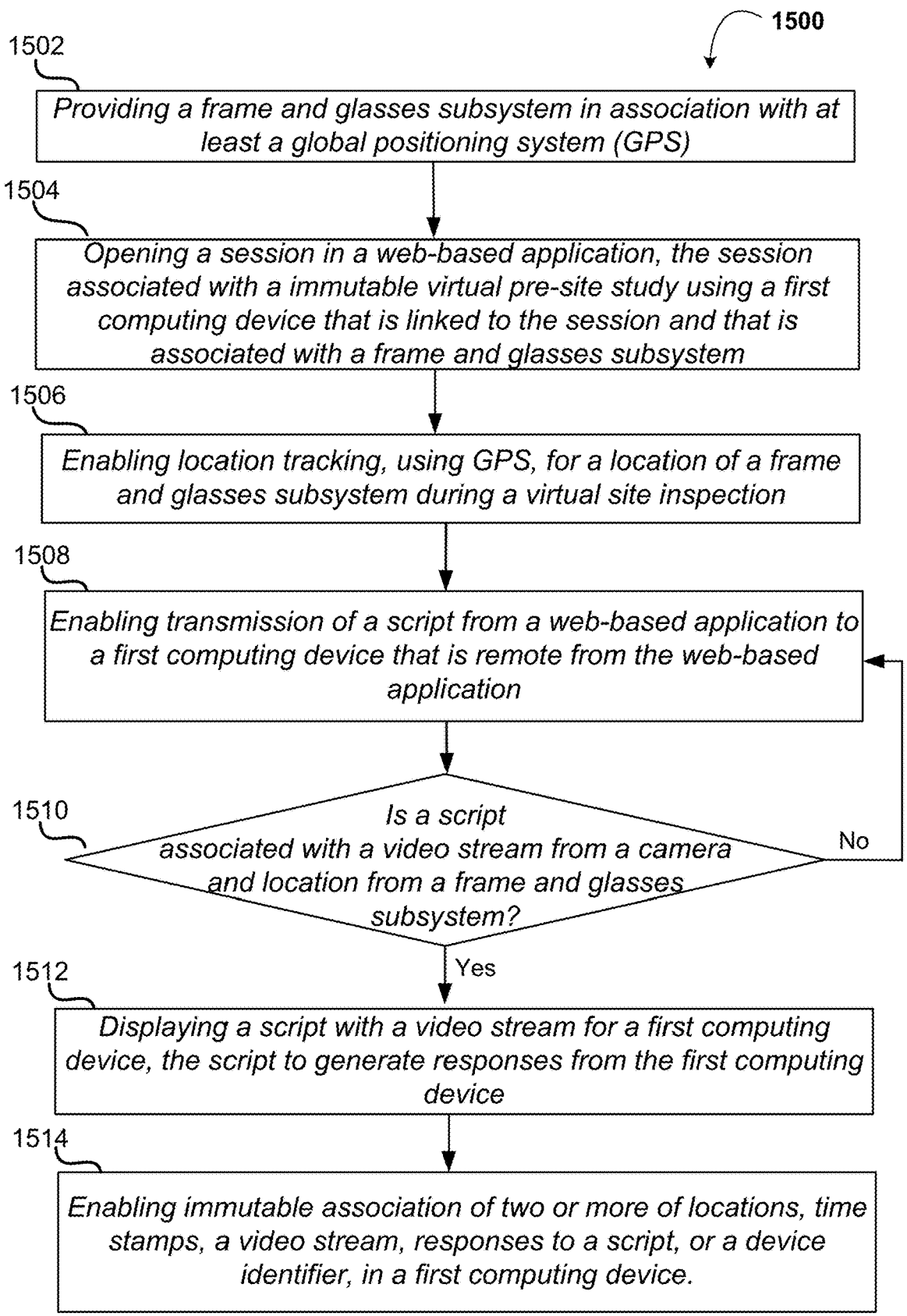
FIG. 15 illustrates a method for an immutable virtual pre-site study according to at least one embodiment herein.

FIG. 15 illustrates another process flow of a method 1500 for immutable virtual pre-site study to support clinical trials. Step 1502 of method 1500 provides a frame and glasses subsystem in association with at least a global positioning system (GPS). Step 1504 is for opening a session in a web-based application. The session may be associated with an immutable virtual pre-site study using a first computing device that is linked to the session and that is associated with the frame and glasses subsystem. Step 1506 is for enabling location tracking, using the GPS, for a location of the frame and glasses subsystem during the immutable virtual pre-site study. Step 1508 is for enabling transmission of a script from the web-based application to the first computing device. The first computing device is remote from a second computing device that interfaces with the web-based application. The interfacing may be by displaying a web-based application on a display of the second computing device and by receiving input in the second computing device to effect changes to at least a script within the web-based application or a different form application. The script may be associated with a video stream from a camera of the frame and glasses subsystem and with the location. The association may occur automatically by target insertion points identified for questions in the script.

Step 1510 is for determining if a script is associated with a video stream and with a location. Step 1512 may be performed when this is the case. Step 1508 may be otherwise repeated. Step 1512 is for displaying the script with the video stream for the first computing device, which may occur when GPS coordinates track to the target insertion points in the script. The script is to also generate responses from the first computing device, such as by responses provided by a study coordinator a resident of the research site. Step 1514 is for enabling immutable association of two or more of locations, time stamps, the video stream, the responses to the script, or a device identifier, in the first computing device. For example, time stamps may be tagged or added to a video stream to indicate that a location was visited and that responses to the script are associated with aspects of the location.

In at least one embodiment, an aspect of a location may be an equipment or an inspection action performed at a location. An inspection action may be a measurement of a space, a verification of an equipment, a verification of chemicals, cleaners, or other aspects suitable for an immutable virtual PSSV. The immutable association may be to immediately store such received information under a read-only feature within a first computing device before such received information is transmitted. Furthermore, a file name may be associated with such received information and which may not be changed for a lifetime of the received information. The immutable association may occur within a first computing device but may alternatively occur within a second computing device. A report may be generated with similar immutable features from the first computing device or the second computing device.

A script for an inspection may include aspects of a screen play generated by the form application from the question. The script may be provided to the first computing device for association with location determined from a GPS during an immutable virtual PSSV and to be coordinated with target insertion points marked in the script. In at least one embodiment, with the frame and glasses subsystem and the first computing device playing a script at a research site, a study coordinator has to follow the script and to capture certain information. As such information is captured it may be recorded with time stamps, video stream, responses, and the script, in an immutable manner as a read-only file. Aspects of the script may be changed or overwritten. For example, if a further question exists during the an immutable virtual PSSV (such as relating to a refrigerator at the research site), real-time instructions may be provided to instruct a study coordinator or other person to walk through such a refrigerator unit. Information obtained may be related to inspection dates, size, and still images. As a camera may capture a video stream, time stamping and association a portion of the stream to the specific inspection action—of a refrigeration inspection—enables credible record-taking.

The frame and glasses subsystem herein enable real-time capture of information with the script, responses, and time stamps, in an immutable manner. Furthermore, any verbal discussion may be also captured and synchronized with the video stream and other information gathered. In at least one embodiment, aspects of linking such information and storage in an immutable manner at a source of such information addresses an issue of credibility—such as, to be able to coordinate information communicated between parties during an immutable virtual PSSV to each inspection point at a research site, and to do so in an immutable manner. Merely recording actions distinct from a script, responses, or audio, may lack credibility and may be difficult to stitch together after the fact. Further a requirement to provide this from the source at the time of capture is a technical feature enable by a system and a method of the detailed description herein.

Furthermore, a study coordinator may be disengaged from the responses to questions within the script. This enables an element of privacy and removes bias from the process. Such disengagement may be by capturing information in isolation of sentiment that may raise concerns at the research site. A study coordinator may only follow along with the script and capture information requested in the script. The information is provided directly to a second computing device of the CRA, without commentary to bias its nature. As a study coordinator may be a staff member at the research site and not necessarily a third-party, the study coordinator should not be able to see or alter responses to the questions laid out in the script. For example, the study coordinator may be asked to capture and send certain information beforehand, and during the an immutable virtual PSSV, but such information may not directly correlate to the questions received and may indirectly inform a CRA of capabilities at the research site.

While techniques herein may be subject to modifications and alternative constructions, these variations are within spirit of present disclosure. As such, certain illustrated embodiments are shown in drawings and have been described above in detail, but these are not limiting disclosure to specific form or forms disclosed; and instead, cover all modifications, alternative constructions, and equivalents falling within spirit and scope of disclosure, as defined in appended claims.

What is claimed is:

1. A system for an immutable virtual pre-site study to support clinical trials, the system comprising:
   a frame and glasses subsystem comprising at least a global positioning system (GPS); and at least one processor and memory comprising instructions that when executed by the at least one processor cause the system to:
   open a session in a web-based application, the session associated with the immutable virtual pre-site study using a first computing device that is linked to the session and that is associated with the frame and glasses subsystem;
   enable location tracking, using the GPS, for a location of the frame and glasses subsystem during the immutable virtual pre-site study;
   enable transmission of a script from the web-based application to the first computing device that is remote from a second computing device interfacing with the web-based application, the script to be associated with a video stream from a camera of the frame and glasses subsystem and with the location;
   enable display of the script with the video stream for the first computing device, the script to enable responses from the first computing device;
   enable immutable association of two or more of locations, time stamps, the video stream, the responses to the script, or a device identifier, in the first computing device;
   enable transmission of the locations, the time stamps, the video stream, the responses to the script, and the device identifier to the web-based application from the first computing device; and
   enable immutable storage of the locations, the time stamps, the video stream, the responses to the script, and the device identifier.

2. The system of claim 1, wherein the memory comprising instructions that when executed by the at least one processor further cause the system to:
   enable filtering of the video stream for privacy protection of patient information.

3. The system of claim 1, wherein the memory comprising instructions that when executed by the at least one processor further cause the system to:
   associate the script with an audio stream, the audio stream to be synchronized with the video stream and to be provided to a user of the first computing device or the second computing device.

4. The system of claim 1, wherein the memory comprising instructions that when executed by the at least one processor further cause the system to:
   generate a report comprising the locations, the time stamps, the video stream, the responses to the script, and the device identifier, the report provided from the first computing device or from the web-based application on the second computing device.

5. The system of claim 1, wherein the memory comprising instructions that when executed by the at least one processor further cause the system to:
   enable a first transmission channel between the first computing device and the frame and glasses subsystem to transmit at least the video stream to the first computing device; and
   enable a second transmission channel between the first computing device and the web-based application on the second computing device, the second computing device to enable the transmission of the script for the first computing device.

6. The system of claim 1, wherein the memory comprising instructions that when executed by the at least one processor further cause the system to:
   enable a video session between the first computing device and the web-based application on the second computing device having an open transmission with the first computing device; and
   enable overriding the script by an instruction associated with the video session.

7. The system of claim 1, wherein the memory comprising instructions that when executed by the at least one processor further cause the system to:
   enable a text session between the first computing device and the web-based application on the second computing device having an open transmission with the first computing device; and
   enable overriding the script by an instruction associated with the text session.

8. The system of claim 1, wherein the memory comprising instructions that when executed by the at least one processor further cause the system to:
   enable the session to open in a cloud computing environment;
   associate the first computing device and the second computing device with the session in the cloud computing environment; and
   control entry of third-parties to participate in the session.

9. The system of claim 1, wherein the memory comprising instructions that when executed by the at least one processor further cause the system to:

present the script with the video stream based in part on the locations being associated with inspection actions during the immutable virtual pre-site study; and associate the script with the video stream, the timestamps, and the location immutably prior to transmission from the first computing device to the web-based application.

10. A method for immutable virtual pre-site study to support clinical trials, the method comprising:

providing a frame and glasses subsystem in association with at least a global positioning system (GPS); and opening a session in a web-based application, the session associated with the immutable virtual pre-site study using a first computing device that is linked to the session and that is associated with the frame and glasses subsystem;

enabling location tracking, using the GPS, for a location of the frame and glasses subsystem during the immutable virtual pre-site study;

enabling transmission of a script from the web-based application to the first computing device that is remote from a second computing device interfacing with the web-based application, the script to be associated with a video stream from a camera of the frame and glasses subsystem and with the location;

displaying the script with the video stream for the first computing device, the script to generate responses from the first computing device;

enabling immutable association of two or more of locations, time stamps, the video stream, the responses to the script, or a device identifier, in the first computing device;

enabling transmission of the locations, the time stamps, the video stream, the responses to the script, and the device identifier to the web-based application from the first computing device; and enabling, using a cloud computing environment, immutable storage of the locations, the time stamps, the video stream, the responses to the script, and the device identifier.

11. The method of claim 10, further comprising:
determining patient materials during the video stream; and
filtering the video stream for privacy protection of patient information.

12. The method of claim 10, further comprising:
synchronizing the script with the video stream and with an audio stream based at least in part on the locations of inspection actions during the immutable virtual pre-site study; and displaying the script to a user of the first computing device or the second computing device.

13. The method of claim 10, further comprising:
generating a report comprising the locations, the time stamps, the video stream, the responses to the script, and the device identifier; and
providing the report from the first computing device or from the web based application on the second computing device.

14. The method of claim 10, further comprising:
enabling a first transmission channel between the first computing device and the frame and glasses subsystem to transmit at least the video stream to the first computing device; and
enabling a second transmission channel between the first computing device and the web-based application on the second computing device, the second computing device to enable the transmission of the script for the first computing device.

15. The method of claim 10, further comprising:
enabling a video session between the first computing device and the web-based application on the second computing device having an open transmission with the first computing device; and
overriding the script by an instruction associated with the video session.

16. The method of claim 10, further comprising:
enabling a text session between the first computing device and the web-based application on the second computing device having an open transmission with the first computing device; and
overriding the script by an instruction associated with the text session.

17. The method of claim 10, further comprising:
enabling the session to open in a cloud computing environment;
associating the first computing device and the second computing device with the session in the cloud computing environment; and
controlling entry of third-parties to participate in the session.

18. The method of claim 10, further comprising:
presenting the script with the video stream based in part on the locations being associated with inspection actions during the immutable virtual pre-site study; and
associating the script with the video stream, the timestamps, and the location immutably prior to transmission from the first computing device to the web-based application.

* * * * *